United States Patent [19]
Bar-Am et al.

[11] Patent Number: 6,043,039
[45] Date of Patent: Mar. 28, 2000

[54] METHOD OF AND COMPOSITE FOR IN SITU FLUORESCENT HYBRIDIZATION

[75] Inventors: Irit Bar-Am, Herzlia, Israel; Cathy Janish, San Diego, Calif.; Yuval Garini, Koranit, Israel; Dario Cabib, Timrat, Israel; Robert A. Buckwald, Ramat Yishay, Israel

[73] Assignee: Applied Spectral Imaging, Migdal Haemek, Israel

[21] Appl. No.: 09/122,661

[22] Filed: Jul. 27, 1998

Related U.S. Application Data

[63] Continuation-in-part of application No. 09/025,131, Feb. 17, 1998, Pat. No. 5,871,932.
[51] Int. Cl.$^7$ .................................................. C12Q 1/68
[52] U.S. Cl. .................................................................. 435/6
[58] Field of Search .................................. 435/6; 536/24.3

[56] References Cited

PUBLICATIONS

Craig et al. Removal of repetitive sequences from FISH probes using PCR–assisted affinity chromotography. Human Genetics vol. 100 pp. 472–476, 1997.

*Primary Examiner*—John S. Brusca
*Attorney, Agent, or Firm*—Mark M. Friedman

[57] ABSTRACT

A fluorescent in situ hybridization method including the steps of (a) obtaining a chromosome spread of a species; (b) preparing a hybridization composite containing a plurality of chromosomal paints each of the plurality of chromosomal paints being labeled with a different fluorophore-or-combination-of-fluorophores, such that an averaged specific activity of highly repetitive sequences in the hybridization composite substantially equals an averaged specific activity of unique sequences in the hybridization composite; (c) denaturing the hybridization composite and subjecting the hybridization composite to conditions for allowing at least a part of the highly repetitive sequences in the hybridization composite to reanneal while at least a part of the unique sequences in the hybridization composite remaining single stranded; (d) contacting under hybridization conditions the hybridization composite with the chromosome spread; (e) washing away excess of the hybridization composite; and (d) analyzing and presenting images of the now hybridized chromosome spread.

66 Claims, 39 Drawing Sheets

(37 of 39 Drawing Sheet(s) Filed in Color)

METHOD OF AND COMPOSITE FOR IN SITU FLUORESCENT HYBRIDIZATION

This is a continuation-in-part of U.S. patent application Ser. No. 09/025,131, filed Feb. 17, 1998 U.S. Pat. No. 5,871,932.

FIELD AND BACKGROUND OF THE INVENTION

The present invention relates in general to karyotyping via fluorescent in situ hybridization. More particularly, the present invention relates to a method of and a composite for fluorescent in situ hybridization using a hybridization composite of chromosomal paints which is free of added unlabeled highly repetitive DNA, such as Cot-I fraction, and which is optionally designed to maximize denaturation and hybridization between DNA probes and target DNAs in cellular samples, thereby enabling reduction of about at least 10–200 fold in concentration of probe employed.

The genome of higher organisms, such as human beings, include a large fraction of repetitive sequences which are spread among all chromosomes. As learned from Cot curves, the human genome may roughly be categorized into (i) highly repetitive sequences, also known as the fast component or the first fraction to reassociate, or Cot-I fraction (Cot=ca. $10^{-4}$ M·sec–ca. $2·10^{-2}$ M·sec, $Cot_{1/2}$=ca. $1.3·10^{-3}$ M·sec), such as, but not limited to, Alu and Alu-like sequences, LINE 1 and 2, sequences, $\alpha$ satellite sequences, $\beta$ satellite sequences, classical satellite sequences, etc.; (ii) intermediate repetitive sequences, also known as the intermediate component (Cot=ca. $2·10^{-1}$ M·sec–ca. $10^2$ M·sec, $Cot_{1/2}$=ca. 1.9 M·sec), such as, but not limited to, ribosomal DNA; and (iii) low repetitive and unique sequences, also known as the slow component, or the last fraction to renature (Cot=ca. $10^2$ M·sec–ca. $10^4$ M·sec, $Cot_{1/2}$=ca. $6.3·10^2$ M·sec), such as, but not limited to, gene encoding sequences. Additional details concerning these fractions of the human genome are described in, for example, Genes V, Benjamin Lewin, Oxford University Press. (1994) pp. 660–675, which is incorporated by reference as if fully set forth herein.

Therefore, when a probe including repetitive sequences, such as a chromosomal paint, is hybridized with target DNA also including repetitive sequences, such as a chromosome spread, measures must be taken to limit or reduce hybridization of the labeled repetitive sequences from the probe with the repetitive sequences in the target DNA.

These measures may include one or more of the following: (i) removal of the repetitive sequences from the probe; (ii) blocking the repetitive sequences of the probe by addition of unlabeled repetitive sequences in excess to the probe composite and providing annealing conditions underwhich substantially only repetitive sequences hybridize, typically by limiting hybridization time; and/or (iii) blocking the repetitive sequences of the target DNA by addition of unlabeled repetitive sequences in excess to the target DNA during the prehybridization procedure. When fluorescent in situ hybridization is envisaged, blocking the repetitive sequences of the probe is currently accepted as the method of choice, yielding best results.

However, all of these methods call for additional time consuming steps and must be executed very precisely for good results.

The use of fluorescent dyes (i.e., fluorescent probes, fluorophores, fluorochromes), is one of the most powerful and common tools for analyzing tissues and cells. Fluorescence microscopy is therefore one of the most important experimental methods used in light microscopy [Lakowicz (1983) Principles of fluorescence spectroscopy, Plenum Press, New York, London].

The power of fluorescent probes, is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason, editor (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated fluorescent dye molecules continues to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

An important example where the detection of multiple fluorescent probes can be of significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities associated with genes and/or chromosomes.

Certain diseases and disorders, including many cancers and birth defects, are genetic disorders caused by defects (i.e., mutations) in one or more genes. Many other diseases arc known or believed to have a genetic component(s), that is, there exists a genetic defect(s) that does not alone cause the disease but contributes to it, or increases the probability of developing the disease later in life, phenomena known in the art as multifactorial diseases and genetic predispositions.

Correlation of visible genetic defects with known diseases would allow physicians to make definitive diagnoses, and permit early detection and treatment of many diseases. Genetic counseling could alert prospective parents and at-risk individuals to the possibility of potentially serious medical problems in the future, permitting appropriate intervention.

More than 8,000 genetic disorders have now been identified, many of which are associated with multiple genetic defects. Following the discovery that chromosomes are the carriers of hereditary information, scientists reasoned that it should be possible to document visible defects in chromosomes that were responsible for specific disorders.

In the 1960's, staining techniques were developed for microscopy-based classification of metaphase chromosomes spreads. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes), deletions (missing chromosome(s) or fragment(s) thereof), additions, inversions and other defects that cause deformities and genetic diseases. Yet conventional chromosome banding techniques are limited in resolution.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes.

The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (i) FISH can be used not only on isolated chromosomes and nucleus, but also whole cells within fixed, paraffin-embedded tissue sections; (ii) it can detect relatively small defects (ability of detecting smaller defects constantly increases); (iii) it can provide results relatively fast; (iv) its moderate cost allows it to be used in most diagnostic and research laboratories; (v) adaptation can be developed for various probes and specimen types; and, (vi) high specificity and sensitivity can be achieved; (vii) within a short time, in some cases in the range of two hours.

Many FISH applications merely require from the cytogeneticist to look through the eyepieces of a microscope, or at the image on the monitor, and to determine whether a fluorescent label is present or absent. With somewhat more complex specimens, a simple count of one or two colored labels may be done. However, the ability to process digital images and extract numerical data from them adds a vast new set of capabilities to FISH techniques.

An appropriate imaging method, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag, count the number of copies present of each targeted chromosome and detect structural changes. Locus-specific probes are used to map the location of small regions of genetic material. These types of probes can be used on intact interphase nucleus as well as metaphase chromosome spreads, and can be counted visually or automatically by a suitable algorithm. They are routinely used to identify genetic diseases characterized by numerical and/or structural changes in chromosomes and/or gene.

Using FISH it is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the fragments. Whole chromosome probes, also known as chromosome paints, fluorescently label all copies of their target chromosome. One important application of chromosome painting is the detection of translocation of genetic material between two chromosomes, as characteristically occurs in early stages of certain cancers, yet other chromosome aberrations are also detectable.

For example, if chromosome A is specifically labeled with a green paint and chromosome B is labeled with a red paint, translocation of genetic material from A to B will appear as a green area juxtaposed to a red area (and vice versa).

Typically, chromosome paints generated from normal chromosomes are used to detect structural aberrations associated with abnormal (patient) chromosomes. Reverse chromosome painting uses probes generated from an abnormal chromosome to identify DNA from various normal chromosomes which contributed material to the abnormal chromosome.

The method of the present invention, as exemplified hereinbelow in the Examples section, enables to paint the 24 different chromosomes comprising the human karyotype (i.e., genome), each in a different color, and simultaneously detect, identify and meaningfully display a color human karyotype, using a single hybridization procedure followed by a single short measurement.

A remarked improvement in multicolor fluorescent dyes used for labeling chromosome paints is the introduction of combinatorial fluorescent strategies (e.g., combinatorial labeling and combinatorial hybridization) which employ various combinations of few basic fluorescent dyes. For further detail concerning combinatorial hybridization see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (Jan. 1994) Fluoreszenz in situ Hybridizierung in der genetischen Diagnostik, Faculty of theoretical medicine, Ruprecht-Karls University Heidelberg, both are incorporated by reference as if fully set forth herein. For further detail concerning combinatorial labeling see du-Manoir et al. (1993) Detection of complete and partial chromosome gains and losses by comparative genomic in situ hybridization. Hum. Genet. 90, 590–610, and U.S. Pat. No. 5,759,781 to Ward et al., both are incorporated by reference as if fully set forth herein.

Numerous methods are available to label DNA probes for use in FISH (including chromosome painting) assays, including indirect methods whereby a hapten such as biotin or digoxigenin is incorporated into DNA using enzymatic reactions. Following hybridization to a metaphase chromosome spread or interphase nucleus, a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes and combinations thereof, known in the art as combinatorial labeling. Alternatively, a pool of a given probe may be divided into sub-pools, each labeled with a different fluorophore, after which the sub-pools are regrouped to yield otherwise similar hybridization results, a method known in the art as combinatorial hybridization. According to both labeling strategies obtained are combinatorial probes. Thus, when any of the terms "combination of fluorophores" is used herein in this document and especially in the claims below, it refers both to combinatorial labeling and to combinatorial hybridization, as described above.

The use of combinatorial fluorophores for chromosome painting and karyotyping, multicolor chromosome banding and comparative genome hybridization is described in details in U.S. Pat. No. 5,817,462 in U.S. Pat. No. 5,759,781 to Ward et al. and in Science magazine [E. Schroeck et al. (1996) Multicolor spectral karyotyping of human chromosomes. Science, 273, 494–497], all are incorporated by reference as if fully set forth herein.

The main progress described in Science is that whole genome scanning by spectral imaging allows instantaneous visualization of defined emission spectra for each human chromosome after fluorescence in situ hybridization (FISH). By means of computer separation (classification) of spectra, spectrally-overlapping chromosome-specific DNA probes are resolved and all human chromosomes are simultaneously identified.

This spectral imaging approach therein described combines Fourier spectroscopy, charge coupled device (CCD)-imaging, and optical microscopy to measure simultaneously at all points in the sample emission spectra in the visible and near-infrared spectral range. This allows the use of multiple spectrally overlapping probes. The approach is based on the measurement of a discrete spectrum (identified from a sequence of intensities at every pixel measured at many different wavelengths), which facilitates the discrimination of multiple fluorophores. In dramatic contrast to conventional epifluorescence microscopy in which fluorochrome discrimination is based on the measurement of the fluorescence intensity through a small number of narrow band fluorochrome specific optical filters [see, Speicher et al. (1996) Nature Genetics. 12:368–375], the use of spectral karyotyping, as therein described, allows all the available information present in the emitted photons within the spectrum of emitted light, to be used for analysis.

The spectral-based method for discriminating spectrally overlapping fluorophores (classification) is readily extended to a large number of fluorochromes, provided there are measurable and consistent differences in the emission spectrum of each fluorochrome.

Simultaneous identification of each human chromosome in metaphase preparations, an approach referred to as spectral karyotyping, is also reported. To this end, chromosome-specific composite libraries generated by polymerase chain reaction (PCR) from flow-sorted human chromosomes are directly labeled with nucleotides conjugated to five different fluorophores or combinations thereof A composite probe set containing all 24 chromosomes is then hybridized to metaphase chromosomes. Chromosome-specific labeling is achieved by suppression hybridization. Specifically, repetitive sequences in the hybridization composite are blocked by the addition of an excess of unlabeled human Cot-I DNA.

The hybridization is presented in both RGB display and classification colors. Display colors allow all human chromosomes to be readily visualized after spectral imaging, and based on spectral measurements at each pixel, a chromosome classification algorithm is applied to spectrally karyotype all human chromosomes. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that the (reference) spectrum of each chromosome has been measured and stored in a reference library in the computer. A distinguishing classification-color is assigned to each pixel in the image according to the classification-color assigned to the reference spectrum that is most similar to the spectrum at that given pixel. A minimal square error algorithm as shown in Equation 1:

$$S_{x,y,n} = \int_{\lambda_1}^{\lambda_2} (I_{x,y}(\lambda) - I_n(\lambda))^2 \, d\lambda \tag{1}$$

is computed for every pixel, in which $I_{x,y}(\lambda)$ is the normalized spectrum at pixel coordinates x,y and $I_n(\lambda)$ represents the normalized reference spectrum for each of the chromosome n=1, 2, . . . , 23, 24. After calculating the value of $S_{x,y,n}$ for all reference spectra, the smallest value is chosen and an artificial classification-color is assigned to that pixel in accordance with the classification-color assigned to the most similar reference spectrum.

The potential of spectral karyotyping as a screening method for chromosomal aberrations was further explored by analyzing clinical samples from multiple laboratories where conventional banding methods or FISH with chromosome painting probes had been previously performed. In all cases, G-banding and spectral karyotyping revealed consistent results. In some cases, Giemsa-banding was not sufficient to entirely interpret the chromosomal aberrations. In these cases, the diagnosis of chromosomal aberrations by spectral karyotyping was confirmed with conventional dual-color FISH analysis. The smallest discernible aberration analyzed for this report was a translocation t(1;11) (q44;p15.3) in which the reciprocal translocation was unrecognizable by conventional banding analysis. The origin of the chromosomal material that contributed to the reciprocal translocation was correctly classified. The translocated segments on chromosomes 1 and 11 had been confirmed by subtelomere specific cosmid probes for chromosomes 1q and 11p. On the basis of the location of the probes utilized, the size of the alteration was estimated to be >1,500 kbp. In a second case, banding analysis suggested a translocation of a segment of chromosome 4 to chromosome 12. Spectral karyotyping unambiguously identified and classified the origin of the additional chromosomal material as being derived from chromosome 4. To determine the limit of sensitivity of spectral karyotyping, a case with a submicroscopic translocation (unrecognizable in both metaphase and prometaphase chromosomes) involving chromosomes 16 and 17 was examined. This t(16;17) had been previously demonstrated by FISH with cosmid probes and the reciprocal interchange of chromatin estimated at approximately 500 kbp. Spectral karyotyping with metaphase chromosomes from this patient failed to identify the known t(16;17) suggesting that the limit of sensitivity for metaphase chromosome analysis with currently available painting probes to be between 500–1,500 kbp.

To demonstrate that spectral karyotyping is an approach that can be used to complement conventional banding analysis, hybridization on previously G-banded chromosomes was performed. Probably due to the trypsin digestion that is required for G-banding, the signal intensity was slightly reduced as compared to metaphases that were not previously G-banded. The loss of signal intensity was approximately 10%, and could therefore easily be compensated for by prolonged exposure times. A slightly increased noise at the edges of previously G-banded chromosomes compared to non G-banded chromosomes was also observed. However, the classification of the metaphase could be readily achieved.

Thus, according to the above described approach, first, chromosomes of a single normal karyotype are identified by a conventional chromosome banding technique (e.g., G-banding or R-banding). Second, the same chromosomes are hybridized with chromosome paints as described above.

Third, the average spectrum characterizing pixels attributed to any chromosome type (e.g., 1–22, X and Y in human male) as previously determined by chromosome banding is calculated and the resulting spectra (e.g., 24 for human) form a library of reference spectra. Fourth, the reference spectra are thereafter used for classification of pixels of new karyotypes into their chromosomes.

The above described results and results by others, see, for example, Speicher et al. (1996) Nature Genetics. 12:368–375, were accomplished by blocking the highly repetitive sequences in the chromosomal paints with excess of unlabeled Cot-I fraction (GIBCO-BRL Life-Technologies, Scotland).

DENHYB™ (DENHYB is a trademark of Ingen Laboratories Inc.) solutions are designed to be used for the suspension or dilution of investigator-developed or commercially available DNA probes. DENHYB™ solutions are developed to maximize denaturation and hybridization between DNA probes and target DNAs in cellular samples. DENHYB™ solutions are compatible with directly and indirectly labeled DNA probes. Two DENHYB™ solutions are available from Sigma depending on the nature of targets or probes:

DENHYB™ (Cat. No. D001): For FISH with repeat sequence (satellite), painting, and also unique sequence probes.

DENHYB™ (Cat. No. D003): Recommended for FISH with unique sequence probes.

DENHYB™ solutions are recommended for use with blocking DNA when both the probe and target include repetitive sequences.

Using DENHYB™ solutions enables to dilute the probes by 10 to 200-fold, depending on the specific application and probe employed, while retaining maximum detection sensitivity. DENHYB™ solutions also reduce hybridization times to between 15 minutes to accomplish FISH on interphase nuclei and metaphase cells with satellite probes. For FISH with paint or unique sequence probes, hybridization for about 3–15 hours is sufficient. Usin DENHYB™, therefore, reduces costs by a large factor.

There is thus a widely recognized need for, and it would be highly advantageous to have a method of and a composite for fluorescent in situ hybridization using a hybridization composite of chromosomal paints which is devoid of added unlabeled highly repetitive DNA sequences.

SUMMARY OF THE INVENTION

According to the present invention there is provided a method and composite for fluorescent in situ hybridization.

According to further features in preferred embodiments of the invention described below, provided is a fluorescent in situ hybridization method comprising the steps of (a) obtaining a chromosome spread of a species; (b) preparing a hybridization composite containing a plurality of chromosomal paints each of the plurality of chromosomal paints being labeled with a different fluorophore-or-combination-of-fluorophores, such that an averaged specific activity of highly repetitive sequences in the hybridization composite substantially equals an averaged specific activity of unique sequences in the hybridization composite; (c) denaturing the hybridization composite and subjecting the hybridization composite to conditions for allowing at least a part of the highly repetitive sequences in the hybridization composite to reanneal, while at least a part of the unique sequences in the hybridization composite remaining single stranded; (d) contacting under hybridization conditions the hybridization composite with the chromosome spread; (e) washing away excess of the hybridization composite; and (d) analyzing and presenting images of the now hybridized chromosome spread.

According to further features in preferred embodiments of the invention described below, provided is a fluorescent in situ hybridization method comprising the steps of (a) obtaining a chromosome spread of a species; (b) preparing an unlabeled-Cot-I free hybridization composite containing a plurality of chromosomal paints each of the plurality of chromosomal paints being labeled with a different fluorophore-or-combination-of-fluorophores; (c) denaturing the hybridization composite and subjecting the hybridization composite to conditions for allowing mostly highly repetitive sequences in the hybridization composite to reanneal while preserving unique sequences in the hybridization composite mostly single stranded; (d) contacting under hybridization conditions the hybridization composite with the chromosome spread; (e) washing away excess of the hybridization composite; and (d) analyzing and presenting images of the now hybridized chromosome spread.

According to still further features in the described preferred embodiments the species is a mammal.

According to still further features in the described preferred embodiments the mammal is a human being.

According to still further features in the described preferred embodiments the hybridization composite contains any number between 1 and all chromosomal paints available for the species.

According to still further features in the described preferred embodiments at least one of the chromosomal paints is a partial chromosomal paint for painting a specific segment of a chromosome.

According to still further features in the described preferred embodiments the hybridization composite further includes excess of unlabeled intermediate repetitive sequences.

According to still further features in the described preferred embodiments the unlabeled intermediate repetitive sequences are ribosomal DNA sequences.

According to still further features in the described preferred embodiments the chromosome spread is of one species and the chromosomal paints are of another species.

According to still further features in the described preferred embodiments the hybridization composite further includes a denaturation agent.

According to still further features in the described preferred embodiments the denaturation agent is formamide.

According to still further features in the described preferred embodiments the hybridization composite further includes a polymer.

According to still further features in the described preferred embodiments the polymer is Dextran sulfate.

According to still further features in the described preferred embodiments the hybridization composite further includes salts.

According to still further features in the described preferred embodiments the salts are SSC.

According to still further features in the described preferred embodiments the averaged specific activities fall within a range of 1–25 fluorophores per 100 nucleotides.

According to still further features in the described preferred embodiments the conditions allowing at least a part of the highly repetitive sequences in the hybridization composite to reanneal are within a range of about 32–36° C. for about 2–4 hours.

According to still further features in the described preferred embodiments the hybridization conditions include a temperature of about 37° C. for a period of time sufficient for the unique sequences of the chromosomal paints to hybridize with their corresponding sequences in the chromosome spread.

According to still further features in the described preferred embodiments the washing step is effected in part by diluted SSC solution.

According to still further features in the described preferred embodiments analyzing and presenting images of the now hybridized chromosome spread is effected by multi-band light collection device or a spectral imager.

According to still further features in the described preferred embodiments the spectral imager includes an interferometer.

According to still further features in the described preferred embodiments each of the chromosomal paints is prepared by labeling with the fluorophores a PCR product derived from a sorted chromosome.

According to still further features in the described preferred embodiments each of the chromosomal paints is prepared by labeling with the fluorophores a sorted chromosome.

According to further features in preferred embodiments of the invention described below, provided is a hybridization composite comprising a plurality of chromosomal paints each of the plurality of chromosomal paints being labeled with a different fluorophore-or-combination-of-fluorophores, such that an averaged specific activity of highly repetitive sequences in the hybridization composite substantially equals an averaged specific activity of unique sequences in the hybridization composite.

According to still further features in the described preferred embodiments highly repetitive sequences in the hybridization composite are mostly annealed, whereas unique sequences in the hybridization composite are mostly single stranded.

According to still further features in the described preferred embodiments when the hybridization composite is allowed to hybridize with a chromosome spread, chromosomes or parts thereof having matching chromosomal paints are labeled and are analyzable via a spectral imager or a multi-band light collection device.

According to still further features in the described preferred embodiments the hybridization composite further comprising a denaturing agent.

According to still further features in the described preferred embodiments the denaturation agent is formamide.

According to still further features in the described preferred embodiments the hybridization composite further comprising a polymer.

According to still further features in the described preferred embodiments the polymer is Dextran sulfate.

According to still further features in the described preferred embodiments the hybridization composite further comprising salts.

According to still further features in the described preferred embodiments the salts are SSC.

According to further features in preferred embodiments of the invention described below, provided is a hybridization composite consisting essentially of a plurality of chromosomal paints each of the plurality of chromosomal paints being labeled with a different fluorophore-or-combination-of-fluorophores, such that an averaged specific activity of highly repetitive sequences in the hybridization composite substantially equals an averaged specific activity of unique sequences in the hybridization composite, wherein highly repetitive sequences in the hybridization composite are mostly annealed, whereas unique sequences in the hybridization composite are mostly single stranded, such that when the hybridization composite is allowed to hybridize with a chromosome spread, chromosomes or parts thereof having matching chromosomal paints are labeled and are analyzable via a spectral imager or a multi-band light collection device, the hybridization composite further consisting of a denaturing agent, a polymer and salts.

According to still further features in the described preferred embodiments each of the chromosomal paints is prepared by labeling with the fluorophores a PCR product derived from a sorted chromosome.

According to still further features in the described preferred embodiments each of the chromosomal paints is prepared by labeling with the fluorophores a sorted chromosome.

According to still further features in the described preferred embodiments the hybridization composite is designed or modified to maximize denaturation and hybridization between DNA probes and target DNAs in cellular samples, thereby enabling reduction of about at least 10–200 fold in concentration of said plurality of chromosomal paints.

According to still further features in the described preferred embodiments the hybridization composite includes a product distributed by Sigma under a name DENHYB™.

According to still further features in the described preferred embodiments the repetitive sequences present in the plurality of chromosomal paints are at least partially removed from the composite, such that they are underrepresented as compared to genomic DNA.

The present invention successfully addresses the shortcomings of the presently known configurations by providing a method of and a composite for unlabeled-Cot-I free in situ hybridization with chromosomal paints.

BRIEF DESCRIPTION OF THE DRAWINGS

The file of this patent contains at least one color photograph. Copies of this patent with color photograph(s) will be provided by the patent and Trademark Office upon request and payment of necessary fee.

The invention herein described, by way of example only, with reference to the accompanying drawings, wherein:

FIGS. 3–5 present hybridization results of 24 chromosomal paints with a normal male chromosome spread using the method and composite according to the present invention, wherein FIG. 3 is an RGB image obtained using an RGB algorithm, FIGS. 4 and 5 are classification images obtained using a classification algorithm, whereas FIGS. 3 and 4 present the original spread and FIG. 5 presents the chromosome spread arranged as a karyotype.

FIGS. 8a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore this result serves as a control. The chromosomal paints were diluted 1:15 in DENHYB solution. The hybridization composite was denatured at 75° C. for 7 minutes and was then left to reanneal for 1 hour at 37° C. Hybridization time was 36 hours. Post wash was with 55% formamide/2× SSC.

C. for 7 minutes and was then left to reanneal for 1 hours at 37° C. Hybridization time was 36 hours. Post wash was with 55% formamide/2× SSC.

FIGS. 20a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 2 hours at 37° C. Hybridization time was 36 hours. Post wash was with 55% formamide/1× SSC.

FIGS. 21a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were not diluted. The hybridization composite was denatured at 75° C. for 7 minutes and was then left to reanneal for 2 hours at 37 ° C. Hybridization time was 36 hours. Post wash was with 55% formamide/1×SSC.

FIGS. 22a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 6 hours at 37° C. Hybridization time was 36 hours. Post wash was with 55% formamide/1× SSC.

FIGS. 23a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:15 in DENHYB solution. The hybridization composite was denatured at 75° C. for 7 minutes and was then left to reanneal for 2 hours at 37° C. Hybridization time was 36 hours. Post wash was with 55% formamide/1× SSC.

Figure 24A:
Figure 24B:

FIGS. 24a–b show an image of human chromosomes, hybridized with chromosome 1 paint. The chromosome paint of FIG. 24b was treated to remove Cot-I sequences via magnetic beads, whereas the chromosome paint of FIG. 24a was not. In both cases prolonged reannealing (4 hours) served to further reanneal still available labeled Cot-I sequences.

Figure 25A:
Figure 25B:
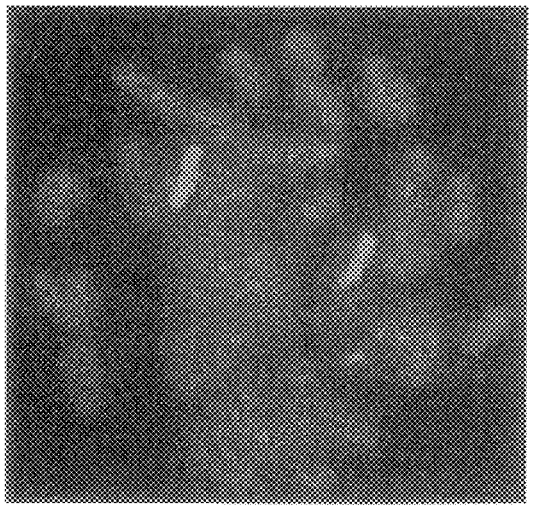

FIGS. 25a–b show an image of human chromosomes, hybridized with chromosome 5 paint. The chromosome paint of FIG. 25b was treated to remove Cot-I sequences via magnetic beads, whereas the chromosome paint of FIG. 25a was not. In both cases prolonged reannealing (4 hours) served to further reanneal still available labeled Cot-I sequences.

DESCRIPTION OF THE PREFERRED EMBODIMENTS

The present invention is of a method and composite which can be used in fluorescent in situ hybridization procedures. Specifically the present invention can be used for providing color (spectral) karyotype, which can be used for detection of chromosomal aberrations.

The principles and operation of the method and composite according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to a preferred embodiment of the present invention there is provided a fluorescent in situ hybridization method which includes the following steps.

First, a chromosome spread of a species is obtained. Obtaining the chromosome spread is preferably effected as described below under Example 1. The species is typically a mammal, such as, but not limited to, a human being.

Second, a hybridization composite is prepared. The hybridization composite contains a plurality of chromosomal paints, each being labeled with a different fluorophore-or-combination-of-fluorophores (see, for example, Table 2 under Example 1 below), such that an averaged specific activity of highly repetitive sequences in the hybridization composite substantially equals an averaged specific activity of unique sequences in the hybridization composite.

According to a preferred embodiment of the present invention, either prior to labeling with the different fluorophore-or-combination-of-fluorophores, or thereafter, repetitive sequences present in the plurality of chromosomal paints are at least partially removed from the composite, such that they are under-represented as compared to genomic DNA. This can be effected, for example, by directly or indirectly binding these sequences to small particulates, such as, but not limited to, magnetic beads, which are thereafter removable, e.g., by a magnetic separator. Other particulates, e.g., arranged in a column or removable by centrifugation are also envisaged, as well known in the art.

Specific activity determines the amount of label (e.g., number of fluorophore molecules) per amount unit of labeled material (e.g., 100 nucleotides of DNA). In the present case, each chromosomal paint employed includes highly repetitive sequences, intermediate repetitive sequences and unique sequences. Each, is labeled with a different fluorophore-or-combination-of-fluorophores. Thus, for example, the specific activity of a given fluorophore in a given paint is defined as the average number of molecules of that fluorophore per 100 nucleotides. Similarly, the average number of molecules of all fluorophore types per 100 nucleotides of types (e.g., repetitive, unique, etc.) of DNA (regardless of their chromosomal origin) in the hybridization composite, defines the averaged specific activity of the types of DNA in the hybridization composite. The phrase "an averaged specific activity" as used herein in the specification and in the claims section below refers to the latter case. The averaged specific activities of the highly repetitive and unique sequences may, for example, fall within a range of 1–25 fluorophores per 100 nucleotides.

The term "substantially" is used herein to indicate possible variation in the averaged specific activities due to, for example, the use of a given type or types of nucleotides for labeling, wherein the highly repetitive sequences differ in their averaged G+C nucleotides content from the unique sequences in the genome studied.

Thus, as already mentioned above, according to the present invention the averaged specific activity of highly repetitive sequences and of the unique sequences in the hybridization composite substantially equals.

Highly repetitive sequences are defined herein as sequences having Cot values ranging between ca. $10^{-4}$–ca. $2.10^{-2}$ M·sec. Unique sequences are defined herein as sequences which appear once in the haploid genome. Highly repetitive sequences can be isolated from genomic DNA by a time limited reannealing procedure and they reflect sequences that fall under the first shoulder of Cot curves, which is known as the Cot-I fraction. A commercial preparation of Cot-I fraction is available from GIBCO-BRL Life-Technologies, Scotland. Typically a Cot-I fraction is added in excess to hybridization composites and serves for blocking labeled highly repetitive sequences therein as described in the Background section above. However, by doing so, the averaged specific activity of the highly repetitive sequences drops to substantially zero.

In other words, the hybridization composite according to the present invention may be regarded to as an unlabeled-Cot-I free hybridization composite which contains a plurality of chromosomal paints each being labeled with a different fluorophore-or-combination-of-fluorophores.

According to a preferred embodiment the hybridization composite contains any number between 1 and all chromosomal paints available for the species, e.g., 24 for human male, 23 for human female. However, according to another preferred embodiment of the invention at least one of the chromosomal paints is a partial chromosomal paint for painting a specific segment of a chromosome, say the long arm of chromosome 1. A segment of a chromosome is defined herein as a part thereof including highly repetitive sequences. Thus, the number of chromosomal paints may be higher than the number of chromosomes and the method as described and claimed may be used for spectral (color) chromosome banding. Furthermore, repetitive blocking sequences free cross-species hybridizations are also envisaged, resulting in a banded painting pattern, as shown, for example, in U.S. Pat. No. 5,817,462, which is incorporated by reference as if fully set forth herein.

According to a preferred embodiment each of the chromosomal paints is prepared by labeling with the fluorophores a PCR, say DOP PCR, product derived from a sorted chromosome. Alternatively, each of the chromosomal paints is prepared by directly labeling with the fluorophores a sorted chromosome.

According to another preferred embodiment of the invention the hybridization composite further includes excess of unlabeled intermediate repetitive sequences, such as, but not limited to, ribosomal DNA sequences. As a result, the averaged specific activity of these sequences in the hybridization composite drops to substantially zero. Addition of, for example, excess of unlabeled ribosomal DNA sequences, ensures, following denaturation and time limited reannealing, that the labeled ribosomal DNA sequences in the composite are blocked (i.e., double stranded) and are therefore not available for inter chromosome hybridizations, e.g., with the telomeres of human chromosomes 13, 14,15, 21 and 22.

According to another preferred embodiment the chromosome spread is of one species (say human) and the chromosomal paints are of another species (say a non-human primate).

As well accepted in the art of hybridizations, the hybridization composite further includes a denaturation agent, such as, but not limited to, formamide; a polymer, such as, but not limited to, Dextran sulfate; and salts, such as, but not limited to, SSC.

Third, the hybridization composite is denatured and is thereafter subjected to conditions allowing at least a part (preferably most, say at least about 70–80%, preferably at least about 85%, more preferably at least about 90%, most preferably at least about 95% or more, ideally about 100%) of the highly repetitive sequences (which are labeled by fluorophores) in the hybridization composite to reanneal, while at least a part (preferably most, say at least about 70–80%, preferably at least about 85%, more preferably at least about 90%, most preferably at least about 95% or more, ideally about 100%) of the unique sequences in the hybridization composite remain single stranded. According to a preferred embodiment of the invention these conditions include reannealing at a temperature in the range of about 20–65, preferably about 30–50° C., more preferably about 35–45° C., for about 2–4 hours, preferably, about three hours.

Fourth, the hybridization composite is contacted under hybridization conditions with the chromosome spread. According to a preferred embodiment of the invention the hybridization conditions include a temperature of about 37° C for a period of time sufficient for the unique sequences of the chromosomal paints to hybridize with their corresponding sequences in the chromosome spread, e.g., 14–48 hours. Further details concerning these conditions are found under Example 1 below.

Fifth, excess of the hybridization composite is washed away. According to a preferred embodiment of the invention washing is effected, in part, by diluted SSC solution, say 0.1× SSC.

Finally, the hybridized chromosome spread is spectrally analyzed and presented as a spectral (color) images. Analyzing and presenting images of the hybridized chromosome spread is effected by a multi-band light collection device or a spectral imager. Preferably, the spectral imager includes an interferometer.

Different approaches of spectral analysis of fluorescent in situ hybridization results are described in, for example, U.S. Pat. Nos. 5,936,731, 5,817,462, 5,835,214, 5,719,024, and 5,798,262, and U.S. application Ser. No. 08/718,831, and in E. Schroeck et al. (1996) Multicolor spectral karyotyping of human chromosomes. Science, 273, 494–497; and Speicher R. M., Ballard S. G. and Ward C. D. (1996) Karyotyping human chromosomes by combinatorial multi-flour FISH. Nature genetics, 12:368–375, all of which are incorporated by reference as if fully set forth herein.

According to a preferred embodiment of the method, the hybridization composite is designed (i.e., in advance, prior to reannealing) or modified (after reannealing as described) to maximize denaturation and hybridization between DNA probes and target DNAs in cellular samples, thereby enabling reduction of about at least 10–200 fold in concentration of said plurality of chromosomal paints. To this end, the hybridization solution is or includes the DENHYB™ solution by distributed by Sigma. The DENHYB™ solution may be used to dissolve the paints and support reannealing. Alternatively, reannealing may be performed as described above, and the reannealed paints diluted in DENHYB™ solution to the desired dilution.

Further according to the present invention there is provided a hybridization composite which includes a plurality of chromosomal paints each being labeled with a different fluorophore-or-combination-of-fluorophores, such that an averaged specific activity of highly repetitive sequences in the hybridization composite substantially equals an averaged specific activity of unique sequences in the hybridization composite.

The hybridization composite is preferably designed or modified to maximize denaturation and hybridization between DNA probes and target DNAs in cellular samples, thereby enabling reduction of about at least 10–200 fold in concentration of said plurality of chromosomal paints. The hybridization composite preferably is or includes a product distributed by Sigma under a name DENHYB™.

According to a preferred embodiment of the invention the repetitive sequences present in the plurality of chromosomal paints are at least partially removed from the composite, such that they are under-represented as compared to genomic DNA.

According to a preferred embodiment of the invention, highly repetitive sequences in the hybridization composite are mostly annealed, whereas unique sequences in the hybridization composite are mostly single stranded.

According to another preferred embodiment, when the hybridization composite is allowed to hybridize with a chromosome spread, chromosomes or parts thereof having matching chromosomal paints are labeled and are analyzable via a spectral imager or a multi-band light collection device.

As well accepted in the art of hybridizations, the hybridization composite further includes a denaturation agent, such as, but not limited to, formamide; a polymer, such as, but not limited to, Dextran sulfate; and salts, such as, but not limited to, SSC.

According to a preferred embodiment each of the chromosomal paints is prepared by labeling with the fluorophores a PCR, say DOP PCR, product derived from a sorted chromosome. Alternatively, each of the chromosomal paints is prepared by directly labeling with the fluorophores a sorted chromosome.

According to another preferred embodiment of the invention the hybridization composite further includes excess of unlabeled intermediate repetitive sequences, such as, but not limited to, ribosomal DNA sequences.

Further according to the present invention there is provided a hybridization composite consisting essentially of a plurality of chromosomal paints each being labeled with a different fluorophore-or-combination-of-fluorophores, such that an averaged specific activity of highly repetitive sequences in the hybridization composite substantially equals an averaged specific activity of unique sequences in the hybridization composite. Highly repetitive sequences in the hybridization composite are mostly annealed, whereas unique sequences in the hybridization composite are mostly single stranded, such that when the hybridization composite is allowed to hybridize with a chromosome spread, chromosomes or parts thereof having matching chromosomal paints are labeled and are analyzable via a spectral imager or a multi-band light collection device. The hybridization composite further consisting of a denaturing agent, a polymer and salts.

According to preferred embodiments of any of the above methods and composites, the hybridization composite is designed to maximize denaturation and hybridization between DNA probes and target DNAs in cellular samples, thereby enabling reduction of about at least 10–200 fold in concentration of the plurality of chromosomal paints employed, depending on the specific application. Thus, preferably, the hybridization composite includes a product distributed by Sigma under the name DENHYB™.

It will be appreciated by one ordinarily skilled in the art that the method and composite according to the present invention are useful not only for fluorescent in situ hybridization, but also to other surface (e.g., filter) hybridizations, wherein both the probe and the target DNA include highly repetitive sequences which may hamper the results.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Reference is now made to the following examples, which together with the above descriptions, illustrate the invention in a non limiting fashion.

EXAMPLE 1

Labeling and Hybridization

Materials:

Materials for PCR: Primer: Telenius 6MW (5'-CCGACTCGAGNNNNNNATGTGG-3', SEQ ID NO:1); Polymerase: Taq (5U/$\mu$l; Promega, M1861); Buffer: 10×PCR Buffer (Promega); Nucleotides: 100 mM dNTPs (Boehringer, 1277049); Dyes: Spectrum Green dUTP (1 mM; Vysis, 30-803200), Spectrum Orange dUTP (1 mM; Vysis, 30-803000), Texas Red dUTP(1 mM; Molecular Probes, 7631), Biotin 16-dUTP (1 mM; Boehringer Mannheim, 1093070), Digoxigenin 11-dUTP (1 mM; Boehringer Mannheim, 1093088); Nucleotides stock solution (Table 1):

TABLE 1

|  | $\mu$l | mM final |
|---|---|---|
| dGTP | 5 | 0.1 |
| dCTP | 5 | 0.1 |
| dATP | 5 | 0.1 |
| dTTP | 3.75 | 0.075 |
| dH$_2$O | 482.25 |  |
| Total | 500 |  |

Materials for precipitation: 20× SSC (Promega, V4261); Dextran Sulfate (Oncor, S4010); Formamide (Oncor, S4117); Sodium Acetate (Peirce); Ethanol absolute (Merck, 100983); Hybridization mix: 2× SSC/20% Dextran sulfate; DENHYB solution (Sigma, 7522).

Material for removal of repetitive sequences: Cot-I DNA (GibcoBRL,15279-011); Biotin Chem Link kit (Boehringer Mannhiem (1812149); Avidin magnetic particels (Boehringer Mannhiem, 1641789).

Materials for pretreatment of chromosome slides: MgCl$_2$, 1M (Sigma, M-1028); Formaldehyde (Merck, 4003); Pepsin: stock solution: 10%=100 mg/ml, PBS/MgCl$_2$: 50 ml of 1M MgCl$_2$ in 950 ml PBS (phosphate buffer saline).

Materials for denaturation and detection: Bovine serum albumin (BSA), fraction V (Boehringer, 735078); Tween 20 (Merck, 109280); Anti digoxin (Sigma, D8156); 60% formaldehyde/2× SSC; 0.1× SSC; 4× SSC/0.1% Tween 20; Blocking Solution: 3% BSA in 4× SSC/0.1% Tween 20; Antibodies dilution solution: 1% BSA in 4× SSC/0.1% Tween 20; Cy5 Avidin (Amersham, PA 45000) 2 mg, Stock solution: 1 mg/ml; Cy5.5 sheep anti mouse (Amersham, RPQ 0115) 1 mg, Stock solution: 1 mg/ml; DAPI (Sigma, D-9542) 1 mg, Stock solution 10 mg/ml; Anti-fade solution: Vectrashield (Vector H-1000).

Methods:

Removal of repetitive sequences: Cot-I DNA was labeled with biotin using a Biotin Chem-Link kit. After labeling (30 min at 85° C.) the products were cleaned using standard Sephadex G50. Flow sorted DNA from each chromosome (300 ng) was added to 15 μl of biotinylated Cot-I DNA and was precipitated therewith. The dried pellet was dissolved in 100 μl of 6× SSC, 0.1% SDS, and was denatured by boiling for 10 minutes, and was left to reanneal at 65° C. overnight. The two DNAs were combined with strepavidin magnetic particles for 30 minutes and then applied to a magnetic particle separator. The supernatant containing the Cot-I under-represented DNA was removed, cleaned and resuspended in 25 μl of TE.

Probe labeling: Flow sorted human chromosomes or Cot-I under-represented human chromosomes were labeled and amplified using DOP-PCR (Telenious 1992). Each chromosome was labeled with 1–4 different fluorochromes conjugated to nucleotides (see Table 2). A total of five different fluorochromes were used: Spectrum Green, Spectrum Orange, Texas Red, Cy5 and Cy5.5. Cy5 and Cy5.5 were indirectly labeled with Biotin and digoxigenin. For each PCR tube 400 ng were combined with 2.5 μl of the appropriate dye according to the labeling scheme (see Table 2).

TABLE 2

| Chromosome No. | Combination |
|---|---|
| 1 | BCD |
| 2 | E |
| 3 | ACDE |
| 4 | CD |
| 5 | ABDE |
| 6 | BCDE |
| 7 | BC |
| 8 | D |
| 9 | ADE |
| 10 | CE |
| 11 | ACD |
| 12 | BE |
| 13 | AD |
| 14 | B |
| 15 | ABC |
| 16 | BD |
| 17 | C |
| 18 | ABD |
| 19 | AC |
| 20 | A |
| 22 | ABCE |
| 23 | AE |
| 24 | CDE |

Key:
A - Spectrum Orange;
B - Texas Red;
C - Cy5;
D - Spectrum Green; and
E - Dig - Cy5.5.

A PCR mixture containing: 1×PCR buffer; 2 mM $MgCl_2$; 10 μl dNTP; 2 μM Primer and 10 Units of Taq DNA polymerase, was added. PCR conditions were: 95° C. for 2 min, 25 cycles of 95° C. for 1 min, 56° C. for 1 min and 72° C. for 4 min, final extension was conducted for 10 minutes at 72° C.

For each hybridization between 0.26 μl (×15 dilution) and 4 μl (no dilution) PCR product from each chromosome were combined together in an epedorf tube and precipitated in the presence of sodium acetate and 100% ethanol without the addition of suppression or carrier DNA (i.e., Cot I free).

According to the "no dilution" procedure, the dry pellet was dissolved in 5 μl of formamide and 5 μl of hybridization stock solution. Final concentration of the hybridization solution was: 50% formamide, 10% Dexran sulfate and 2×SSC.

According to a first "probe dilution" procedure this composition was diluted 10–15 fold in DENHYB solution (after reannealing, see below).

According to a second "probe dilution" procedure, the dry pellet was dissolved in 10 μl of DENHYB solution.

Denaturation and Hybridization: Pretreatment of the slides was carried out according to standard techniques. Briefly, slides were incubated in a 10% pepsin solution for five minutes at 37° C., washed in PBS, fixed in 1% formaldehyde in a $PBS/MgCl_2$ buffer and dehydrated through an ethanol series.

The chromosomes were denatured in 70% formamide/2× SSC at 70° C. for 2 min, then passed through ethanol series and air dried.

According to the "no dilution" procedure, the chromosomal paints cocktail was denatured at 94° C. for 5 min and then incubated at room-temperature —45 ° C, typically at 34° C., for three hours to allow self annealing of the repetitive sequences.

According to the first "dilution" procedure, the chromosomal paints cocktail was denatured at 94° C. for 5 min and then incubated at room-temperature—45° C., typically at 34° C., for three hours to allow self annealing of the repetitive sequences and then diluted 10–15 fold in DENHYB solution.

Whereas, according to the second "dilution" procedure, the chromosomal paints cocktail was denatured at 94° C. for 5 min and then incubated at 40–65° C. for three hours to allow self annealing of the repetitive sequences.

In each case, 10 μl of the chromosomal paints mixture were then applied to the denatured chromosome preparation, covered with a 18×18 mm coverslip, and hybridized for 14–48 h at 37° C.

Detection: The slides were washed in 60% formamide/2× SSC at 45° C. for 15 min, then in 0.1× SSC at 45° C. for 10 min and finally in 4× SSC/0.1% Tween 20 for 4 min. The slides were then blocked with blocking reagent for 30 min, then incubated with Cy5 Avidin and antidigoxigenin (1:200) for 45 min. After washing in 4× SSC/1% Tween 20 at 45° C. additional layer of Cy5.5 anti mouse (1:200) was applied for additional 45 min. The slides were then washed as above and mounted in DAPI/antifade solution.

EXAMPLE 2

The Measurement Apparatus

Figure 1:
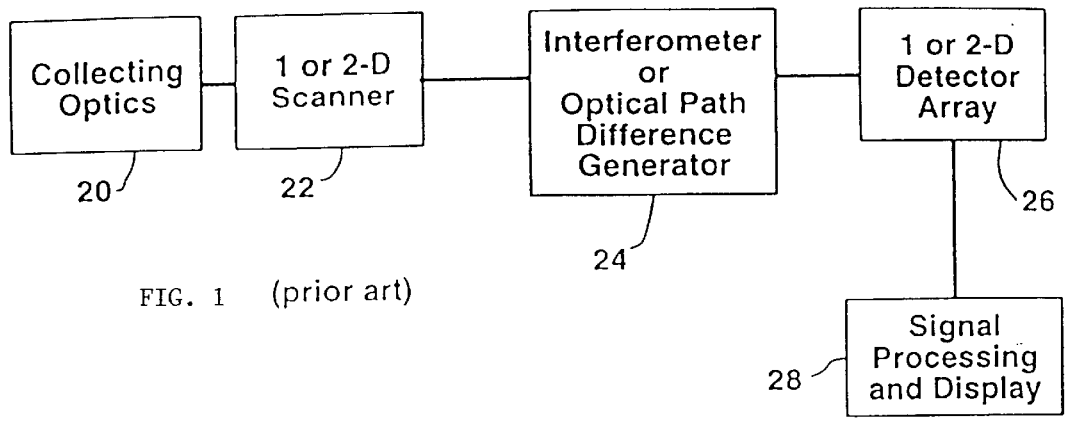
FIG. 1 is a block diagram illustrating the main components of an imaging spectrometer constructed in accordance with U.S. patent application Ser. No. 08/392,019 (prior art)

FIG. 1 is a block diagram illustrating the main components of a prior art imaging spectrometer disclosed in U.S. Pat. No. 5,539,517, issued Jul. 23, 1996, which is incorporated by reference as if fully set forth herein.

This imaging spectrometer is constructed highly suitable to implement the method of the present invention as it has high spectral (Ca. 4–14 nm depending on wavelength) and spatial (Ca. 30/M μm where M is the effective microscope or fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517 alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, such as the four-mirror plus beamsplitter interferometer as further described in the cited U.S. patent (see FIG. 14 there).

Figure 2:
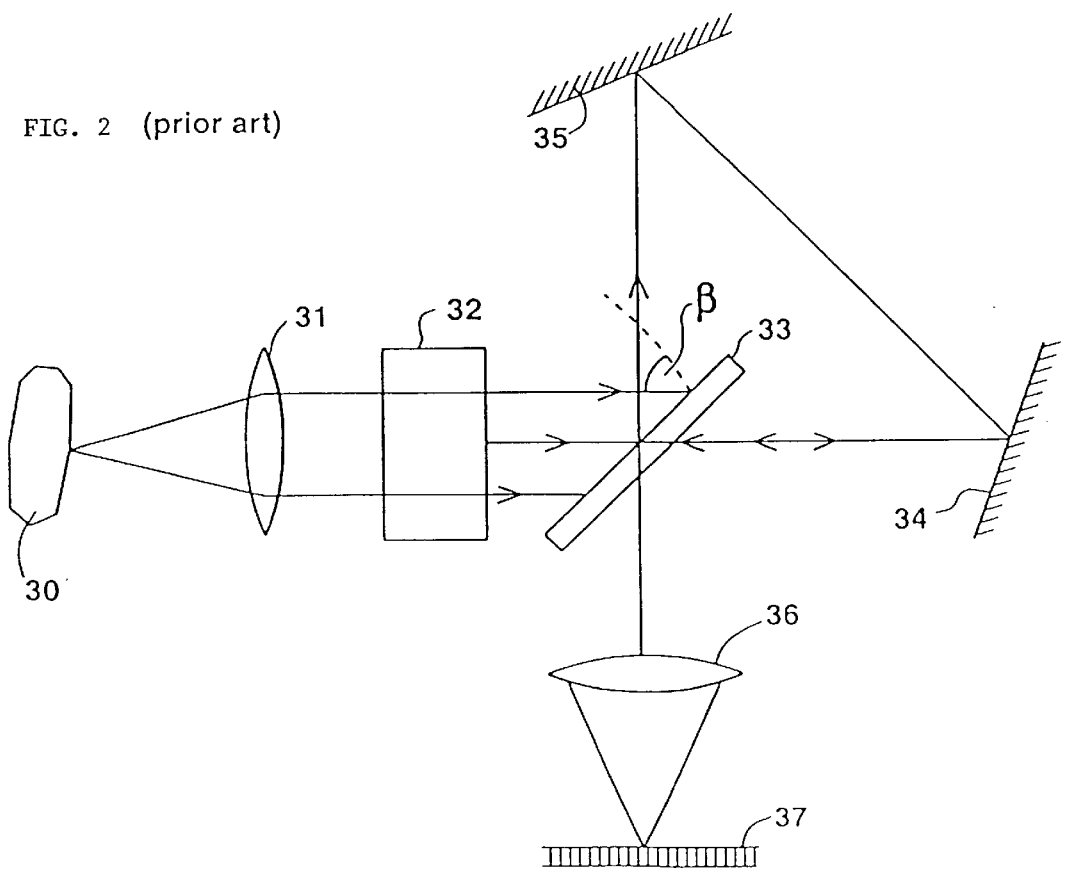
FIG. 2 illustrates a non-moving type interferometer, namely, a Sagnac interferometer, as used in an imaging spectrometer in accordance with U.S. Pat. No. 5,539,517 (prior art)

FIG. 2 illustrates an imaging spectrometer constructed in accordance with U.S. Pat. No. 5,539,517, utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta = 45°$ in FIG. 2) goes through the interferometer with an OPD=0, whereas a ray which is incident at a general angle $\beta - \theta$ undergoes an OPD given by Equation 2:

$$OPD(\beta,\theta,t,n) = t[(n^2 - \sin^2(\beta+\theta))^{0.5} - (n^2\sin^2(\beta-\theta))^{0.5} + 2\sin\beta\sin\theta] \quad (2)$$

where $\theta$ is the angular distance of a ray from the optical axis or interferometer rotation angle with respect to the central position; t is the thickness of the beamsplitter; and n is the index of refraction of the beamsplitter.

It follows from Equation 2 that by scanning both positive and negative angles with respect to the central position, one gets a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SPECTRACUBE™.

The SPECTRACUBE™ system has the following or better characteristics, listed hereinbelow in Table 3:

TABLE 3

| Parameter | Performance |
|---|---|
| Spatial resolution: | 30/M µm (M = effective microscope or fore optics magnification) |
| Field of View: | 15/M millimeters |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–1 80 sec, typical 60 sec |

The SPECTRACUBE™ system optically connected to a microscope is preferably used to analyze the in situ hybridizations according to the present invention. However, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers, or other spectral data or multi-band light collection devices (e.g., a device in accordance with the disclosure in Speicher R. M., Ballard S. G. and Ward C. D. (1996) Karyotyping human chromosomes by combinatorial multi-flour FISH. Nature genetics, 12:368–375) can be used to acquire the required spectral data. Therefore, it is intended not to limit the scope of the present invention for use of any specific type of spectral data collection devices, nor any specific type of spectral imager.

EXAMPLE 3

Karyotyping Results

Figure 3:
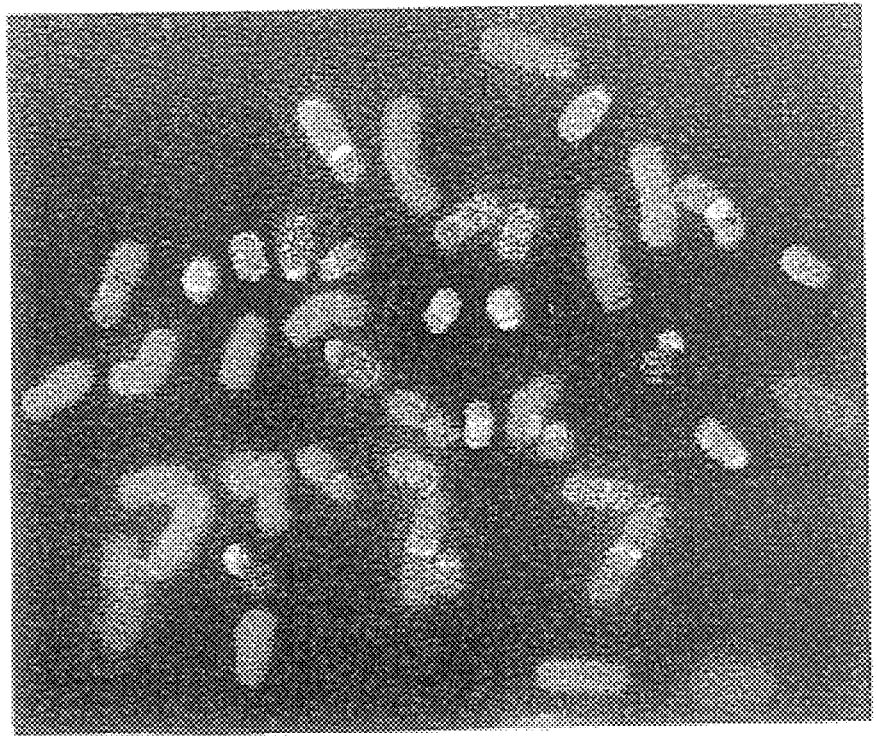
Figure 4:
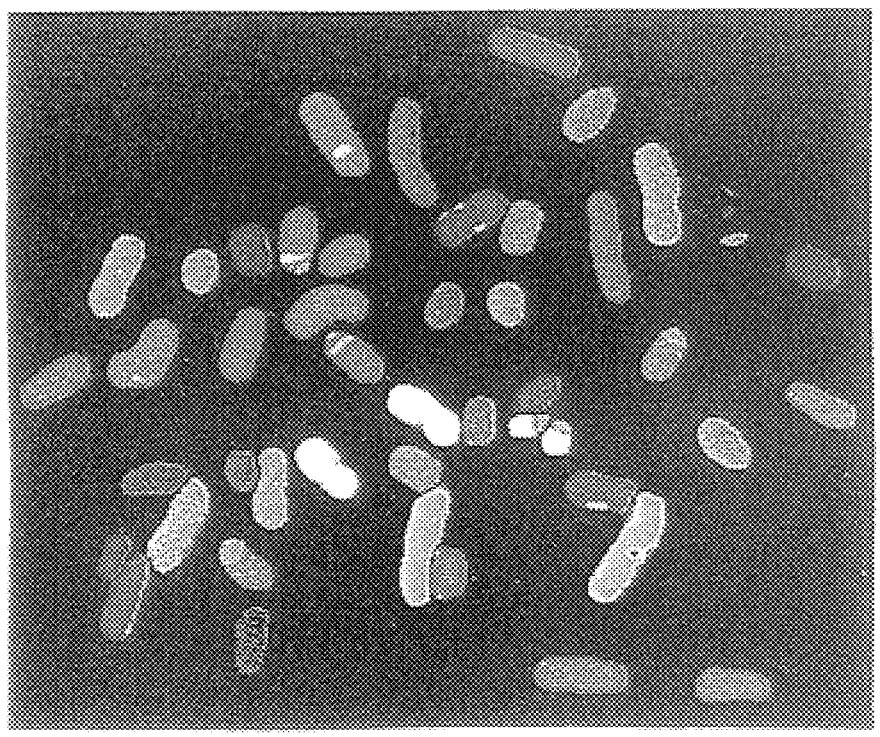
Figure 5:
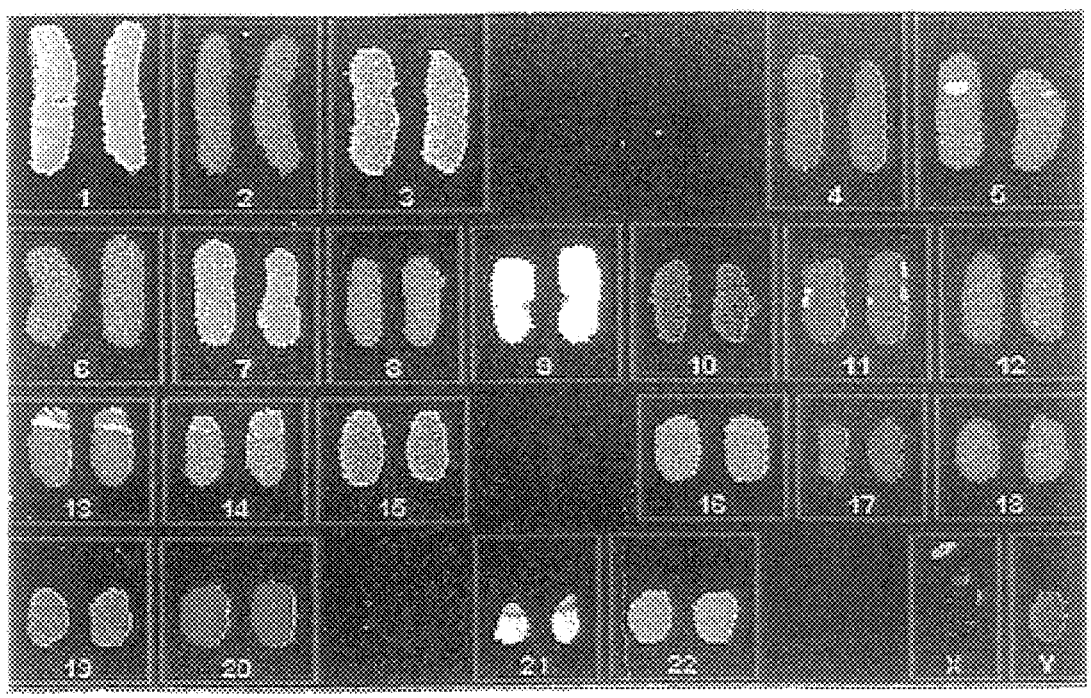

FIGS. 3–5 present hybridization results of normal male chromosomes using the above "no-dilution" protocol (Example 1) and measurement (Example 2).

FIG. 5 is an RGB image of the chromosome spread obtained using an RGB algorithm. The RGB algorithm integrates the optical signal over the spectral range (e.g., 400 nm to 760 nm) of the CCD array to provide an RGB image of the chromosomes, in which each pixel is attributed a combination of red, green and blue intensities according to three weighting functions, $\{w_r(\lambda), w_g(\lambda), W_b(\lambda)\}$, which correspond to the tristimulus response functions for red (R), green (G) and blue (B).

Figure 6:
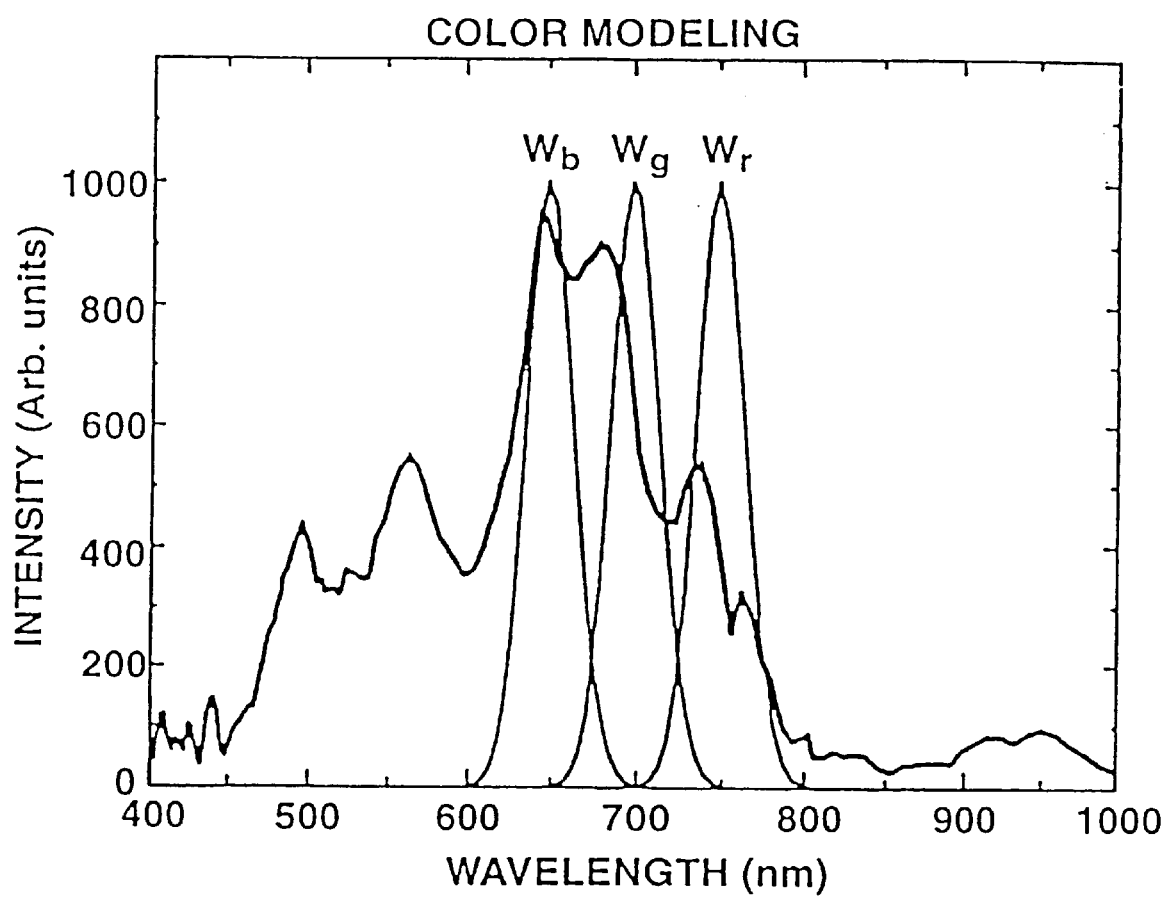
FIG. 6 shows a definition of pseudo-RGB (Red, Green and Blue) colors for emphasizing chosen spectral ranges. The intensity for each pseudo-color is calculated by integrating the area under the curve, after multiplying it by one of the curves.
Figure 7A:
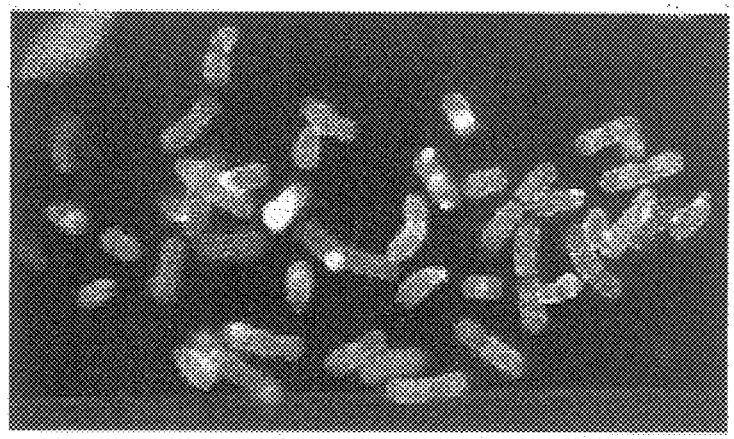
FIGS. 7a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore this result serves as a control. The chromosomal paints were not diluted. The hybridization composite was denatured at 75° C. for 7 minutes and was then left to reanneal for 1 hour at 37° C. Hybridization time was 36 hours. Post wash was with 55% formamide/1× SSC.
Figure 7B:
Figure 7C:
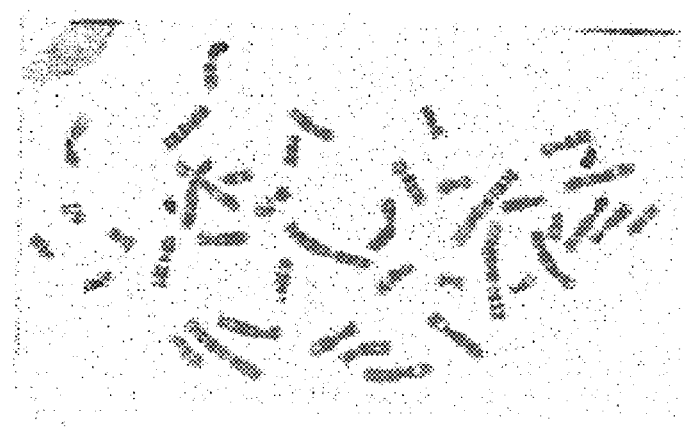
Figure 7D:
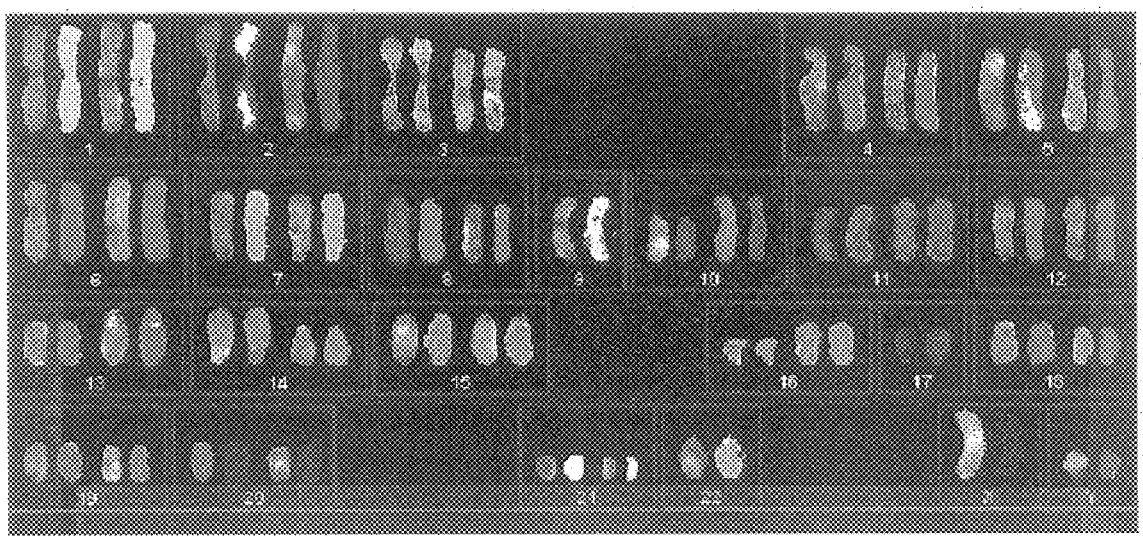
Figure 8A:
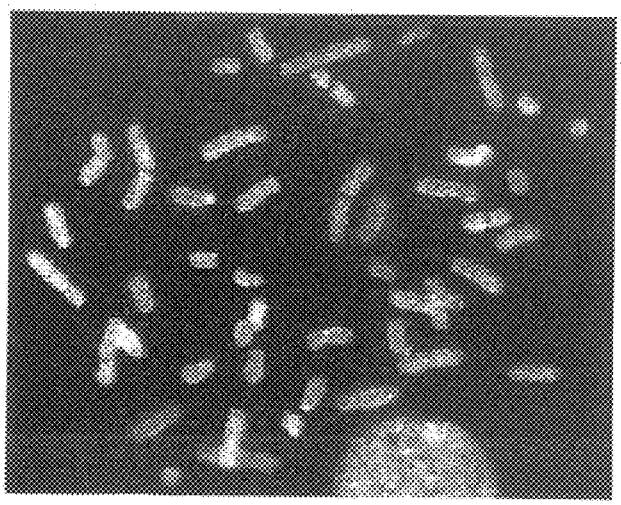
Figure 8B:
Figure 8C:
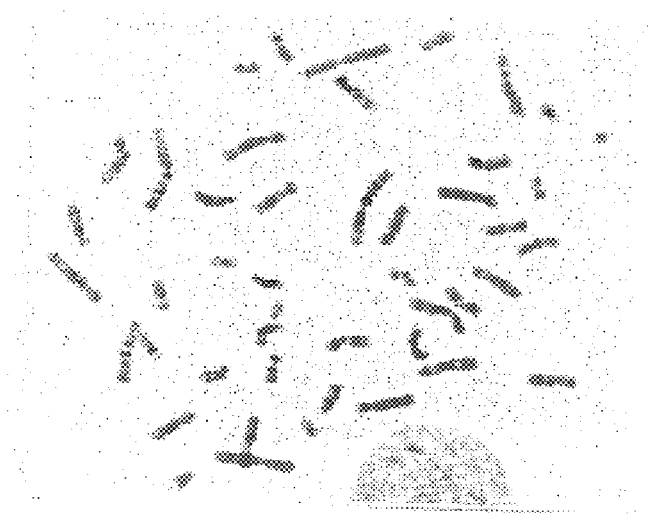
Figure 8A:
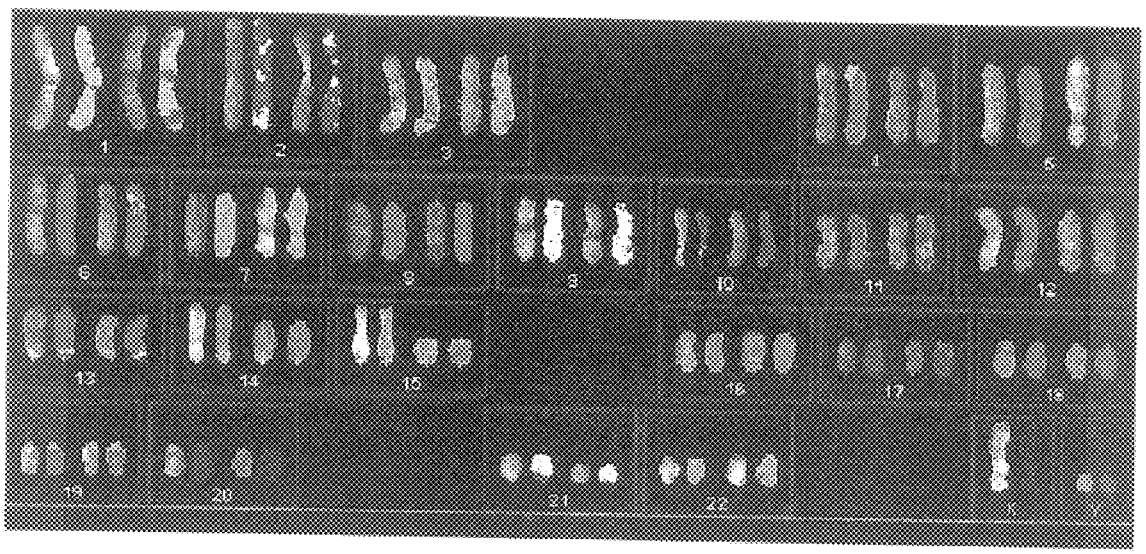
Figure 9A:
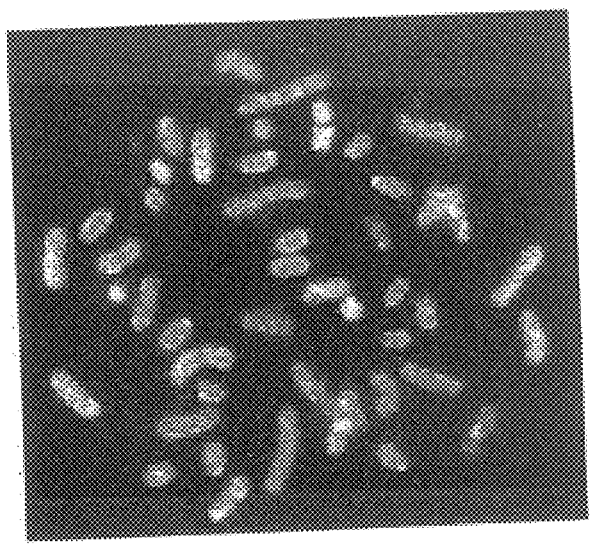
FIGS. 9a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore this result serves as a control. The chromosomal paints were diluted 1:10 in DENHYB solution. The hybridization composite was denatured at 75° C. for 7 minutes and was then left to reanneal for 1 hour at 37° C. Hybridization time was 36 hours. Post wash was with 55% formamide/2× SSC.
Figure 9B:
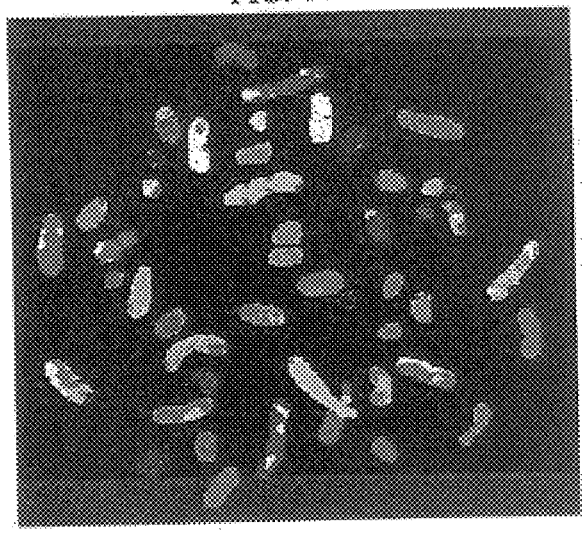
Figure 9C:
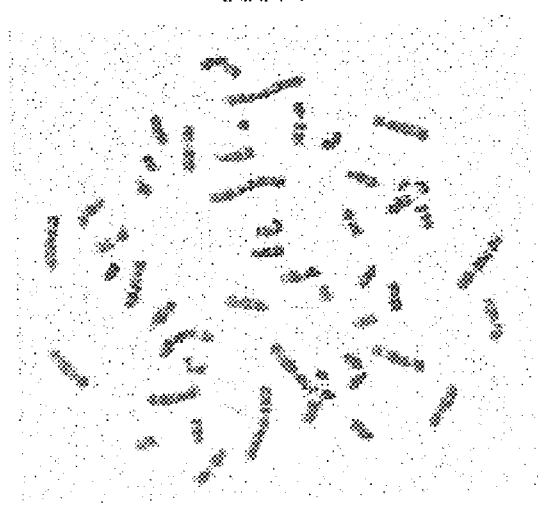
Figure 9D:
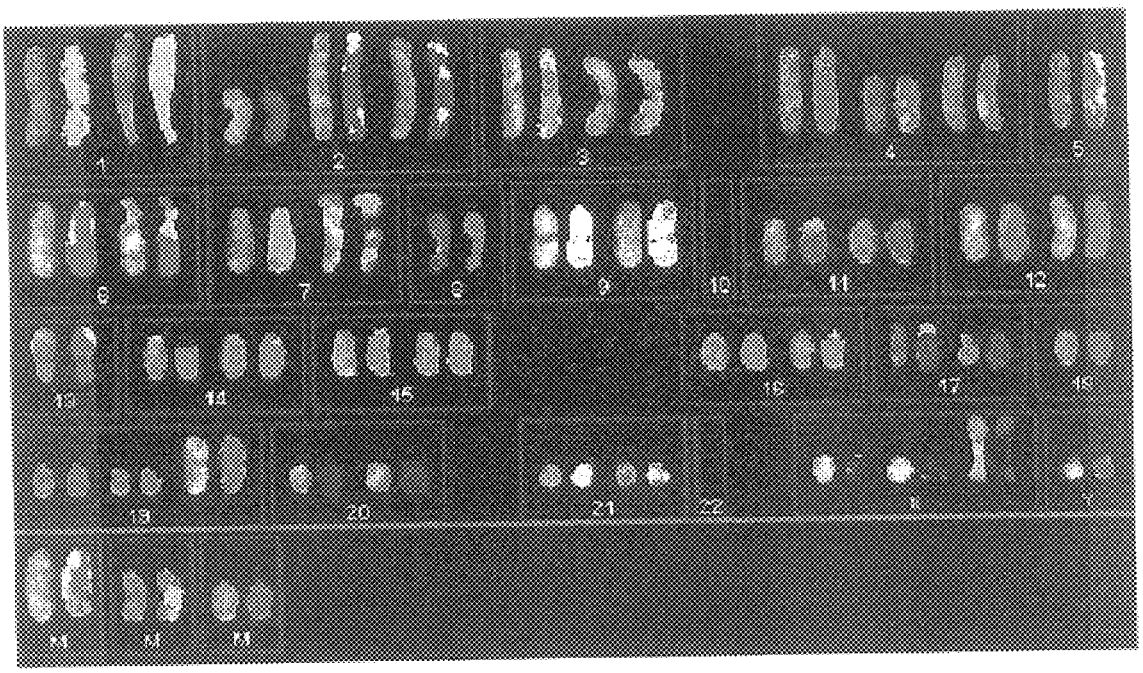
Figure 10A:
FIGS. 10a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 4 hours at 37° C. Hybridization time was 14 hours. Post wash was with 55% formamide/1× SSC.
Figure 10B:
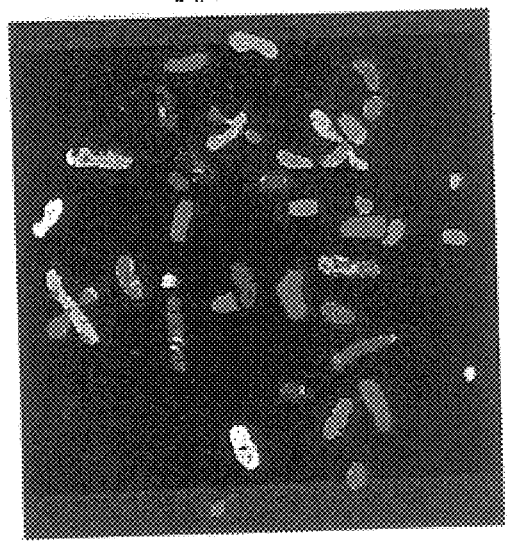
Figure 10C:
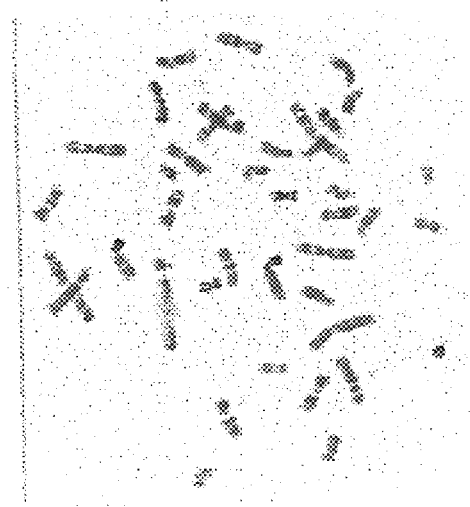
Figure 10D:
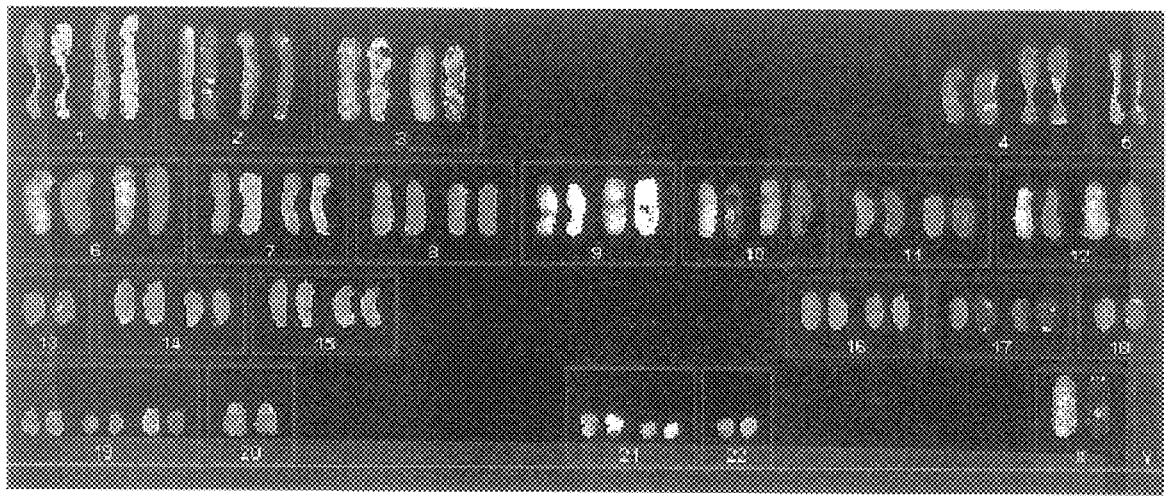
Figure 11A:
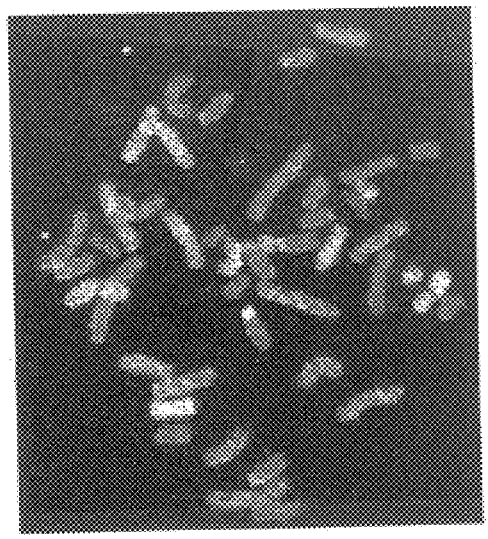
FIGS. 11a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 2 hours at 37° C. Hybridization time was 14 hours. Post wash was with 55% formamide/1× SSC.
Figure 11B:
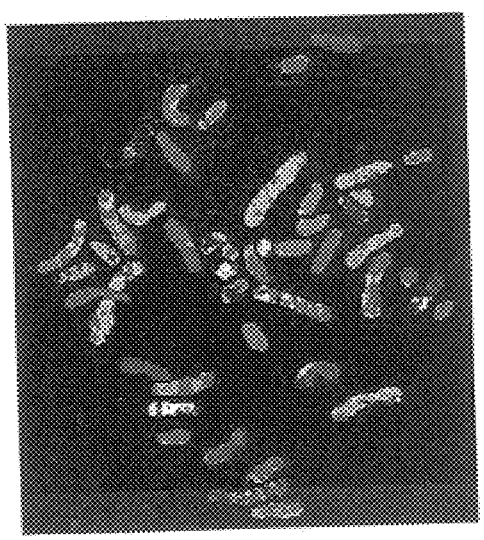
Figure 11C:
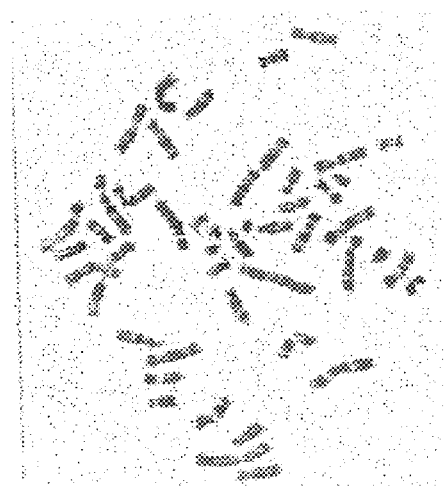
Figure 11D:
Figure 12A:
FIGS. 12a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were not diluted. The hybridization composite was denatured at 75° C. for 7 minutes and was then left to reanneal for 2 hours at 37° C. Hybridization time was 36 hours. Post wash was with 55% formamide/1×SSC.
Figure 12B:
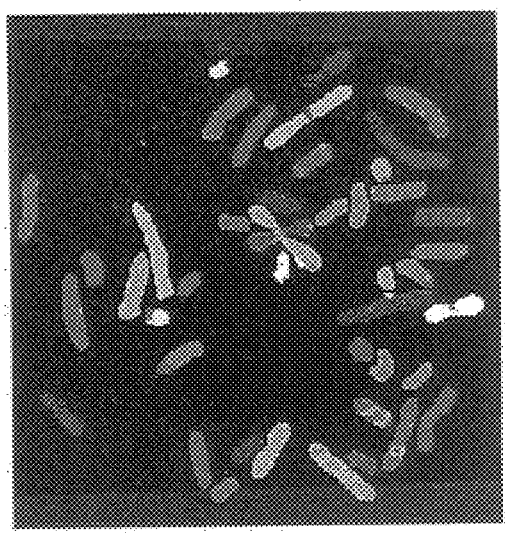
Figure 12C:
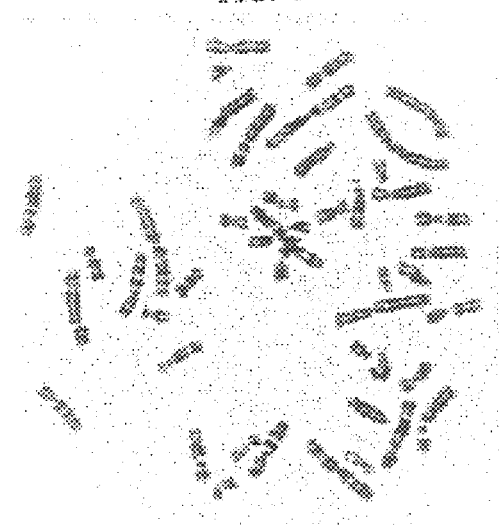
Figure 12D:
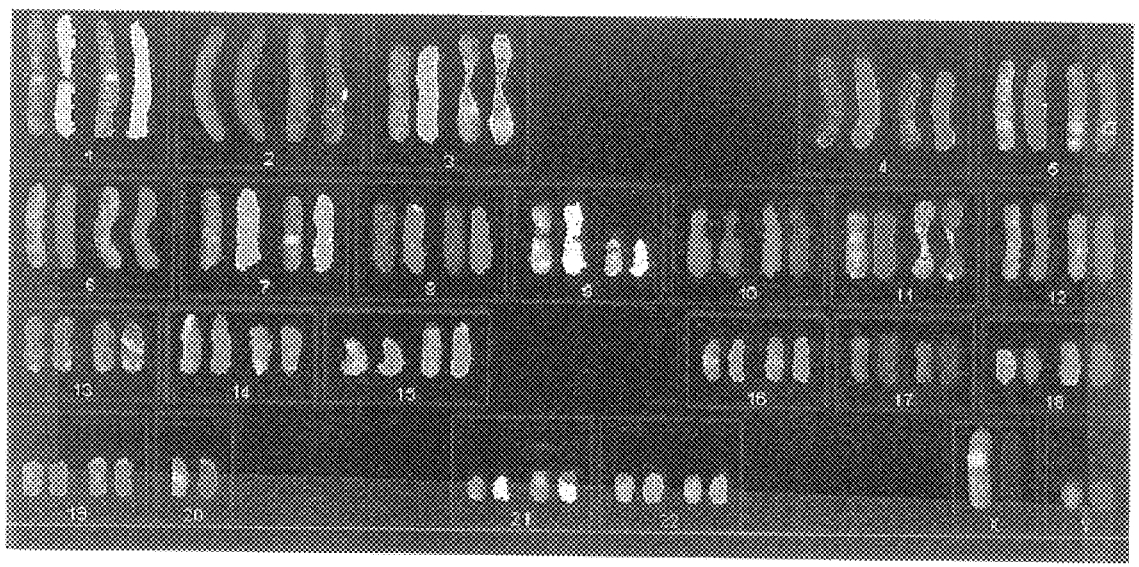
Figure 13A:
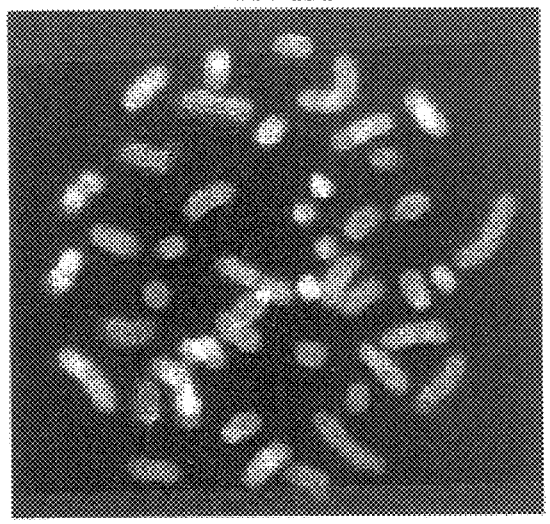
FIGS. 13a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore serves as a control. The chromosomal paints were diluted 1:15 in DENHYB solution. The hybridization composite was denatured at 75° C. for 7 minutes and was then left to reanneal for 1 hour at 37° C. Hybridization time was 36 hours. Post wash was with 55% formamide/2× SSC.
Figure 13B:
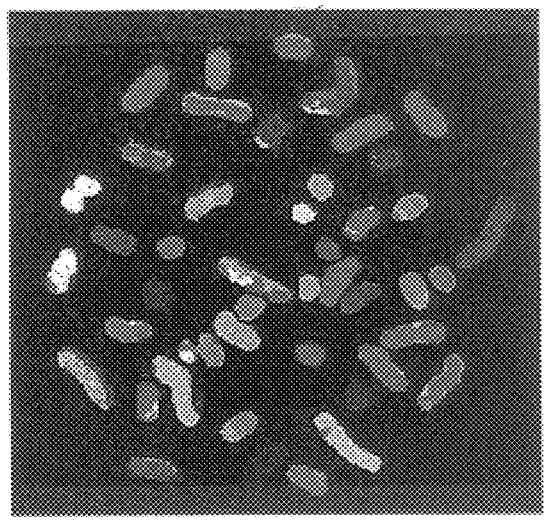
Figure 13C:
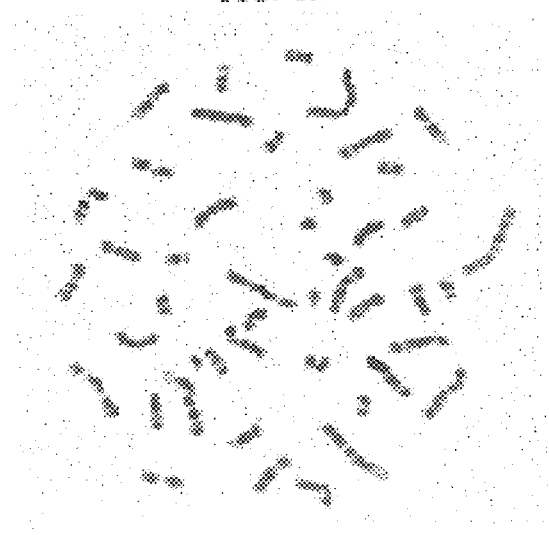
Figure 13D:
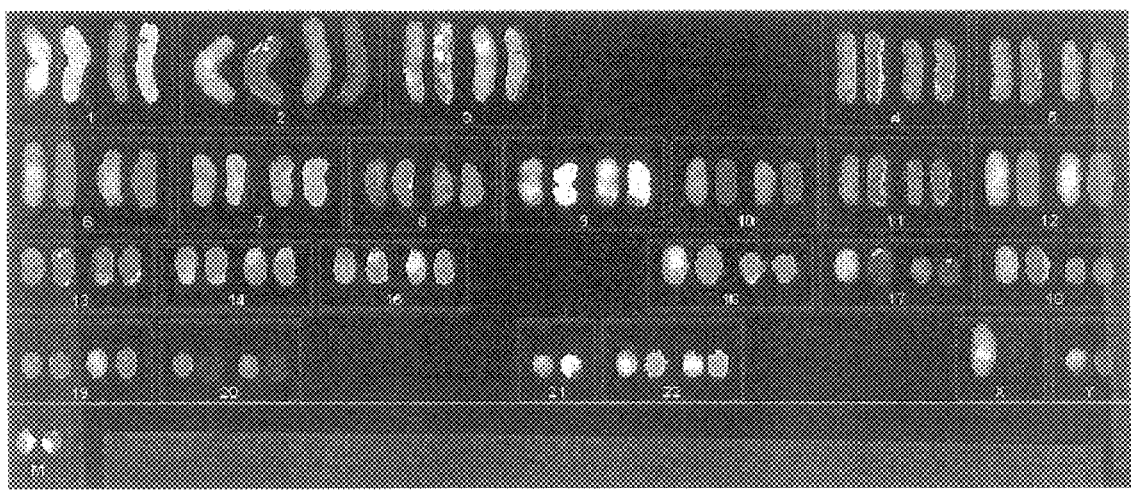
Figure 14A:
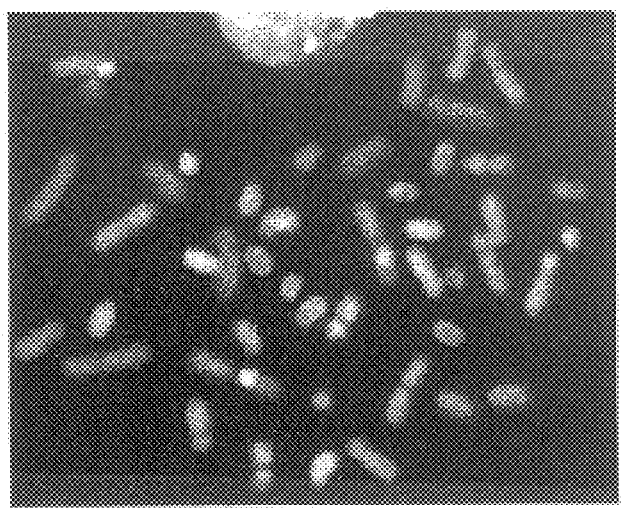
FIGS. 14a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore serves as a control. The chromosomal paints were not diluted. The hybridization composite was denatured at 75° C. for 7 minutes and was then left to reanneal for hour at 37° C. Hybridization time was 36 hours. Post wash was with 55% formamide/1× SSC.
Figure 14B:
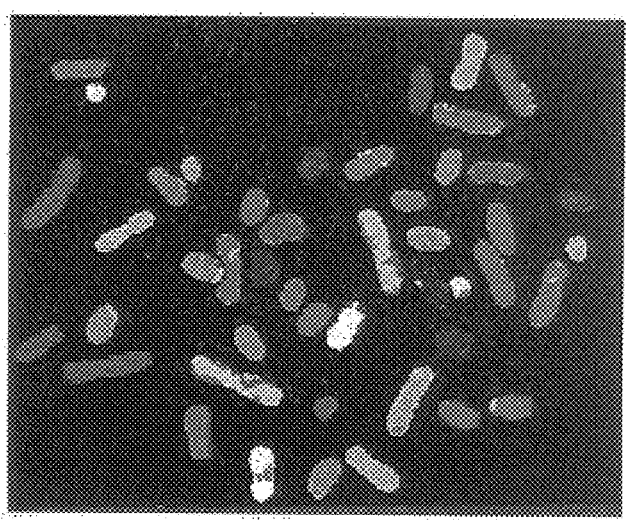
Figure 14C:
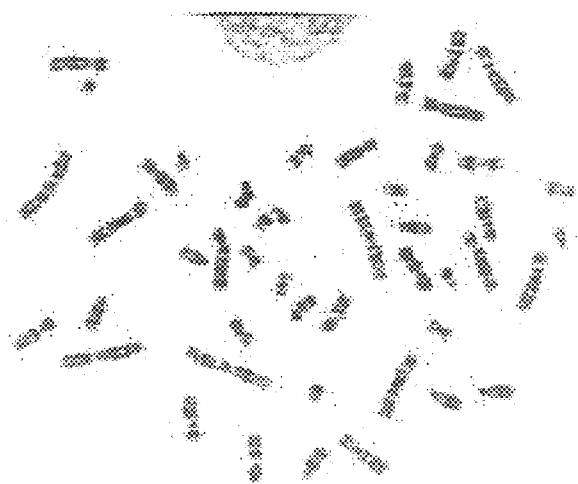
Figure 14D:
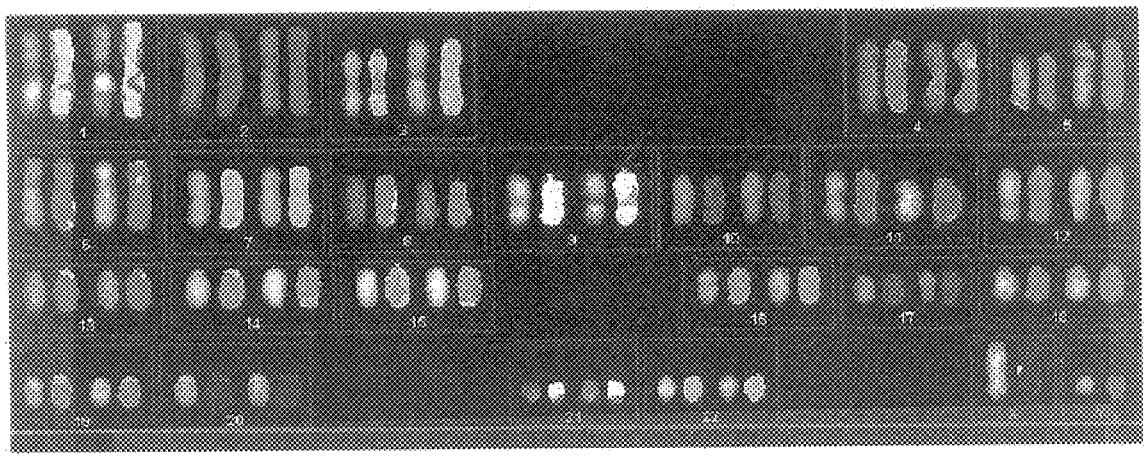
Figure 15A:
FIGS. 15a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore serves as a control. The chromosomal paints were diluted 1:10 in DENHYB solution. The hybridization composite was denatured at 75° C. for 7 minutes and was then left to reanneal for 1 hour at 37° C. Hybridization time was 36 hours. Post wash was with 55% formamide/2× SSC.
Figure 15B:
Figure 15C:
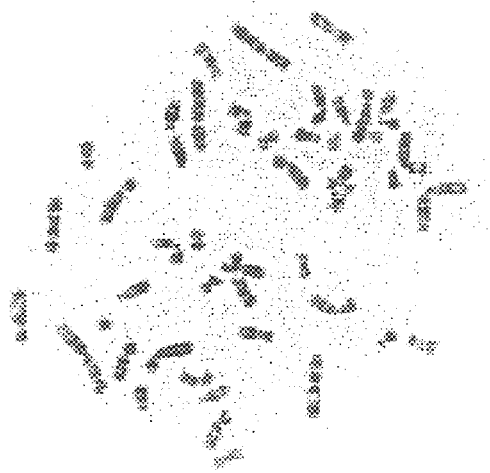
Figure 15D:
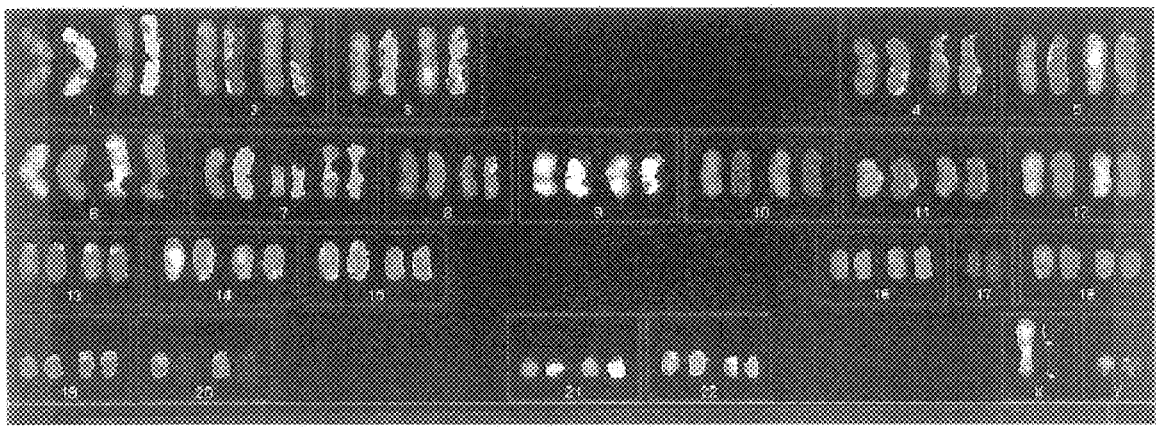
Figure 16A:
FIGS. 16a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 2 hours at 37° C. Hybridization time was 36 hours. Post wash was with 50% formamide/2× SSC.
Figure 16B:
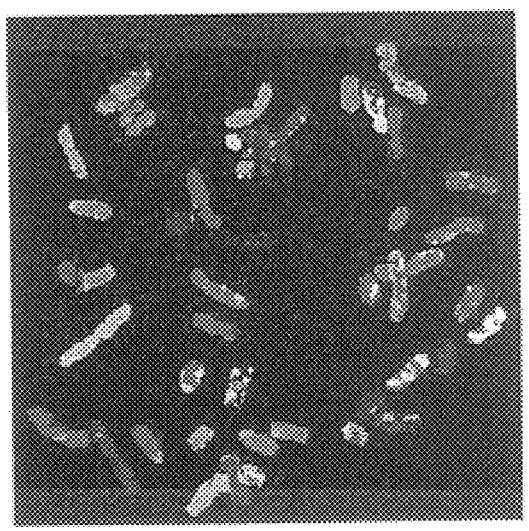
Figure 16C:
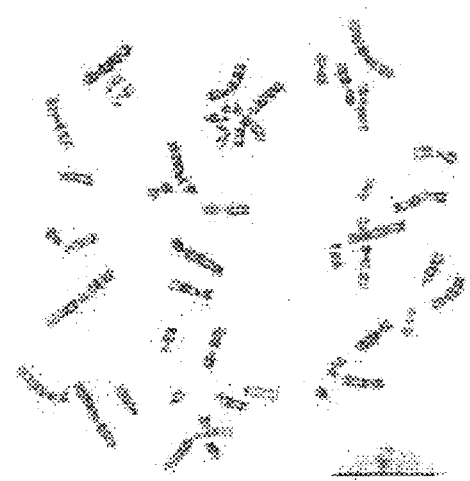
Figure 16D:
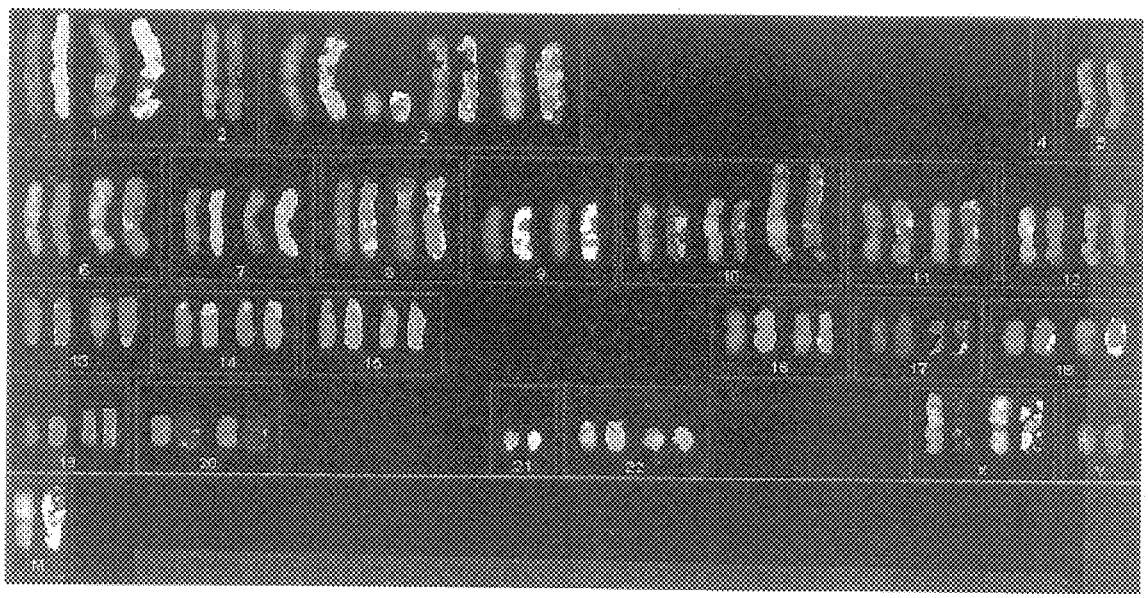
Figure 17A:
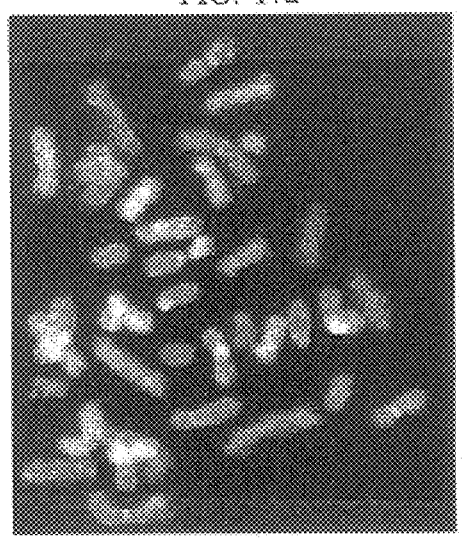
FIGS. 17a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:10 in DENHYB solution. The hybridization composite was denatured at 75° C. for 7 minutes and was then left to reanneal for 6 hours at 37° C. Hybridization time was 36 hours. Post wash was with 55% formamide/1× SSC.
Figure 17B:
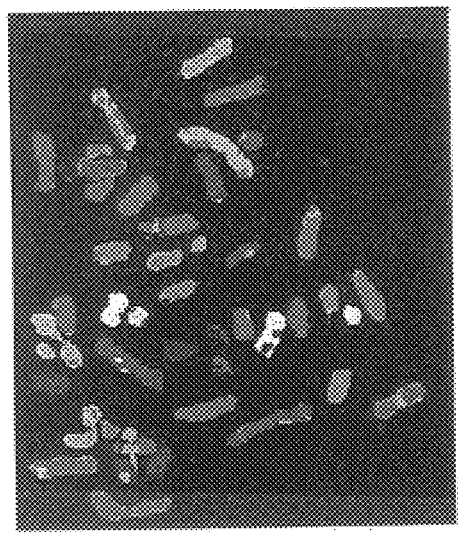
Figure 17C:
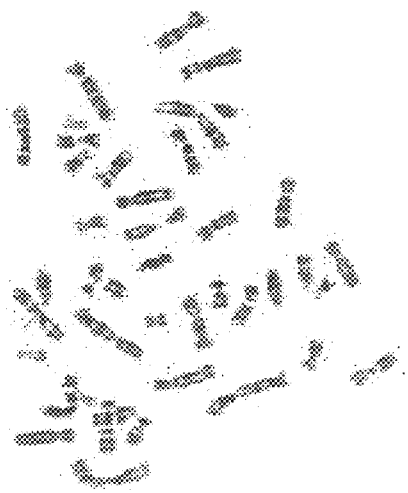
Figure 17D:
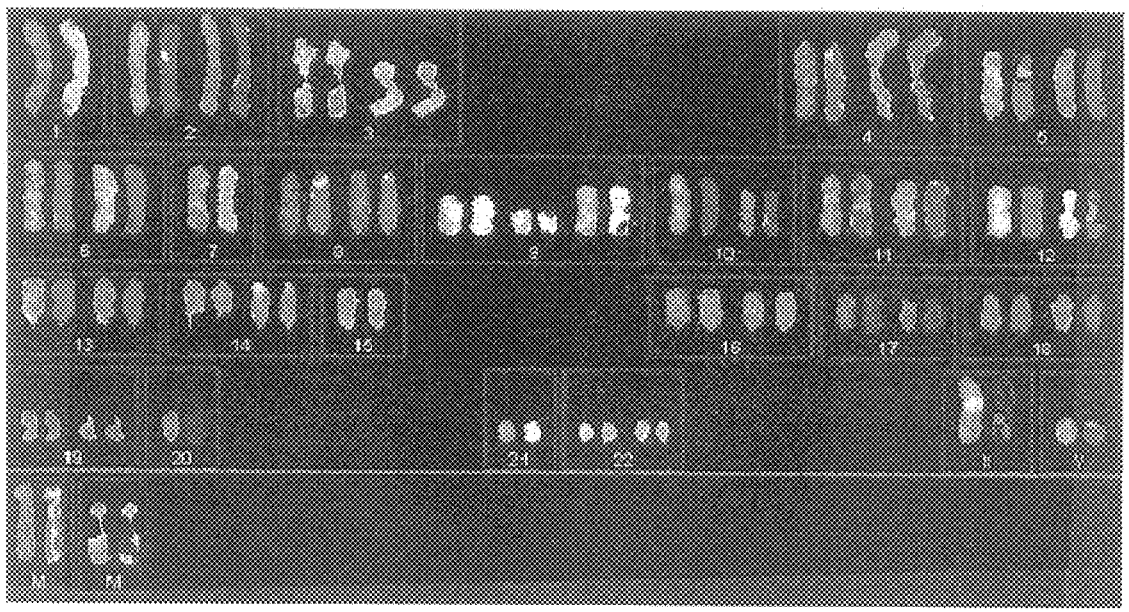
Figure 18A:
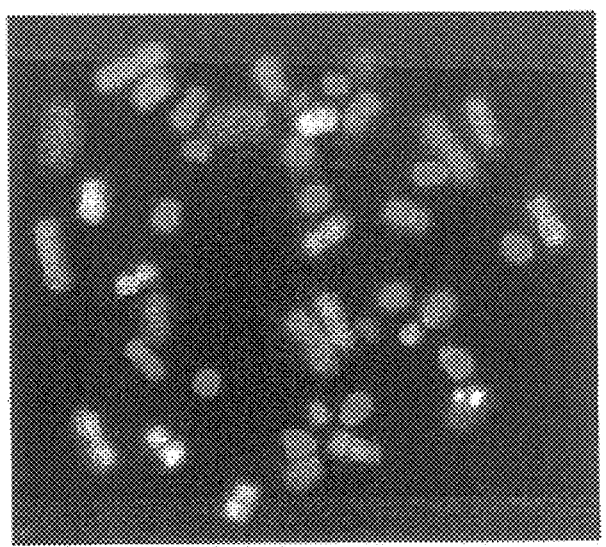
FIGS. 18a–d show a RGB, classification, DAPI and a composite karyotype derived from the RGB and classification images of human male lymphocyte chromosomes, respectively, as retrieved using the SPECTRACUBE system. The hybridization composite in this case did not include Cot-I blocking DNA. The chromosomal paints were diluted 1:15 in DENHYB solution. The hybridization composite was denatured at 75° C. for 7 minutes and was then left to reanneal for 2 hours at 37° C. Hybridization time was 36 hours. Post wash was with 55% formamide/1× SSC.
Figure 18B:
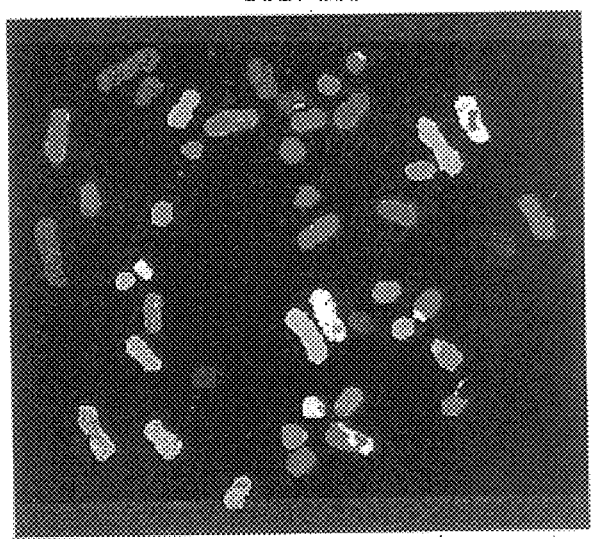
Figure 18C:
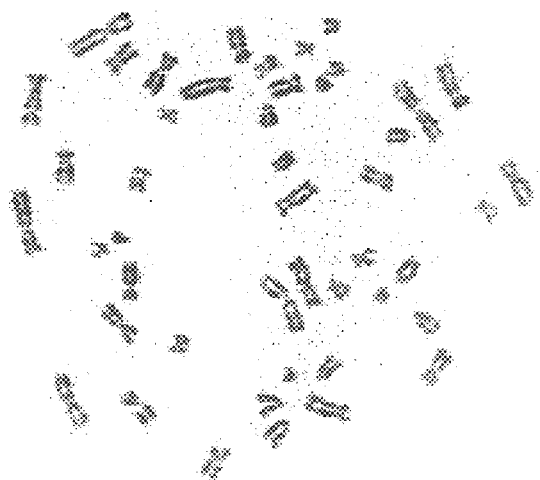
Figure 18D:
Figure 19A:
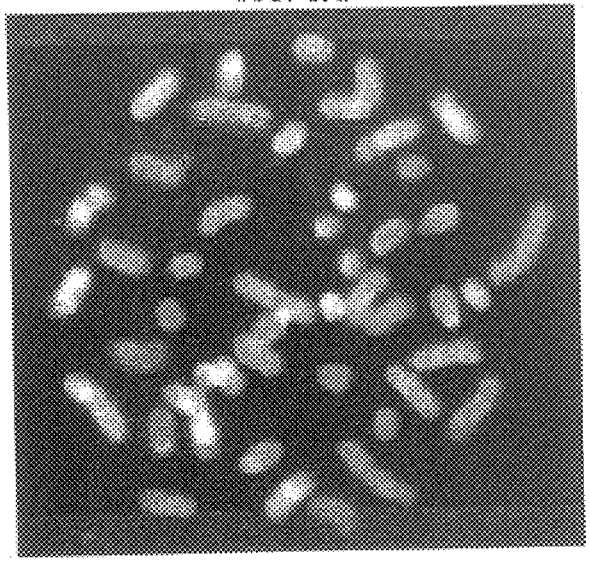
FIGS. 19a–d show a RGB, classification, DAPI and a composite karyotype derived from the RGB and classification images of human male lymphocyte chromosomes, respectively, as retrieved using the SPECTRACUBE system. The hybridization composite in this case included Cot-I blocking DNA and therefore this result serves as a control. The chromosomal paints were diluted 1:15 in DENHYB solution. The hybridization composite was denatured at 75°
Figure 19B:
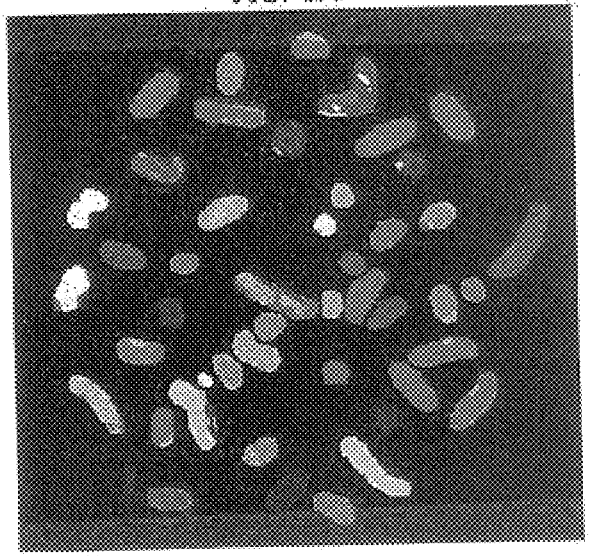
Figure 19C:
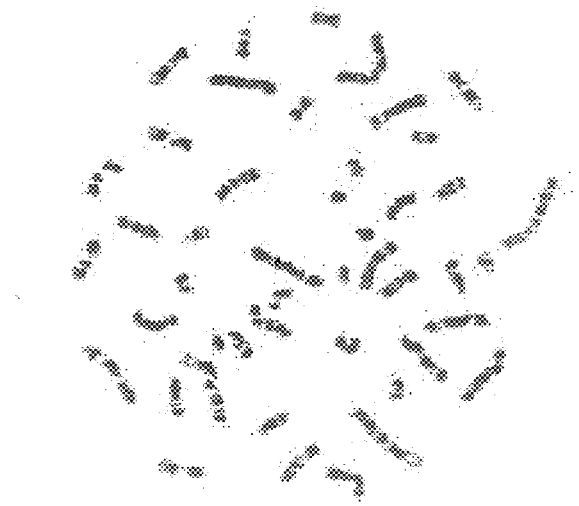
Figure 19D:
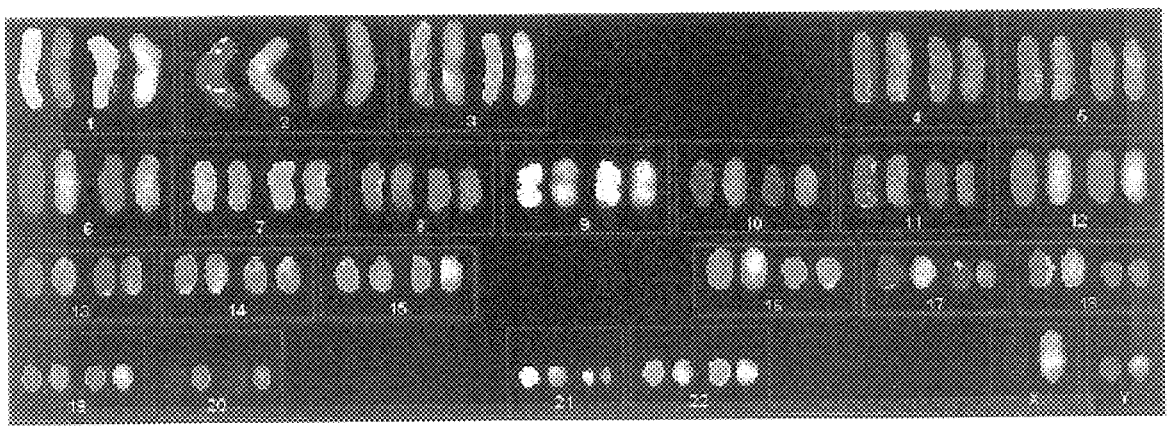
Figure 20A:
Figure 20B:
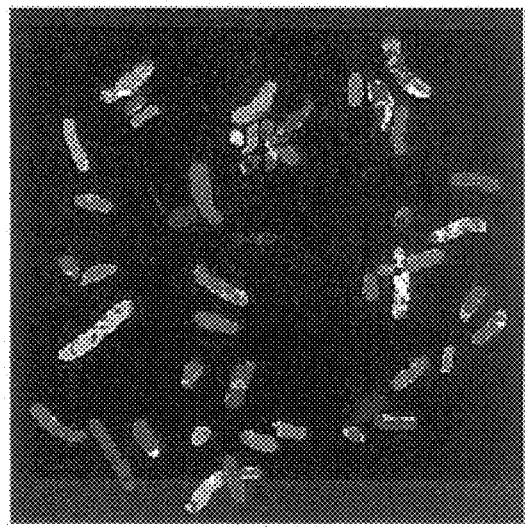
Figure 20C:
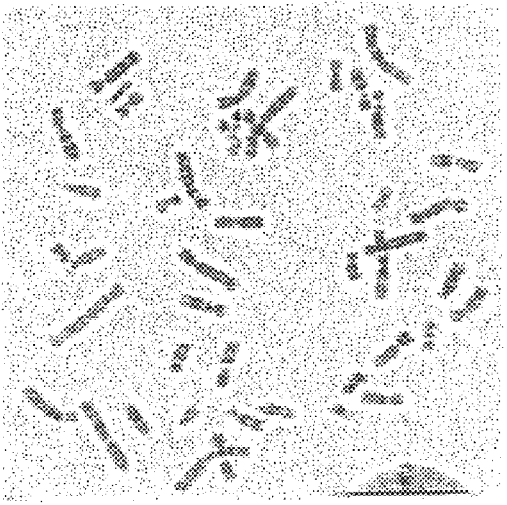
Figure 20D:
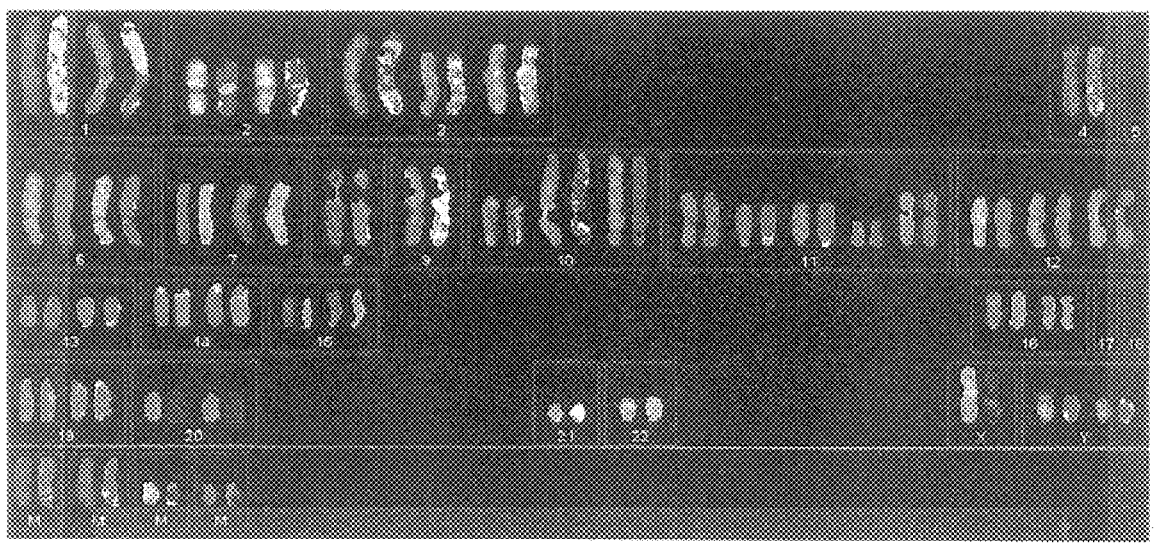
Figure 21A:
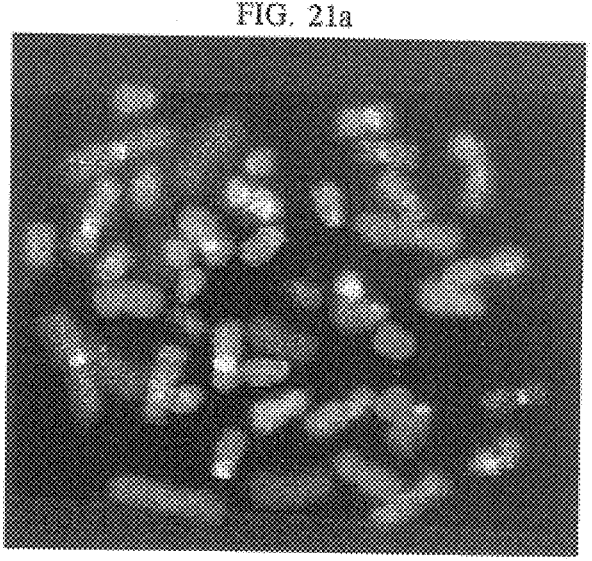
Figure 21B:
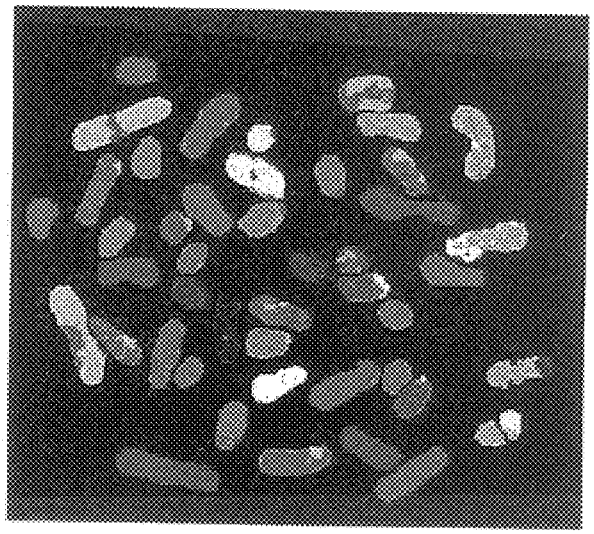
Figure 21C:
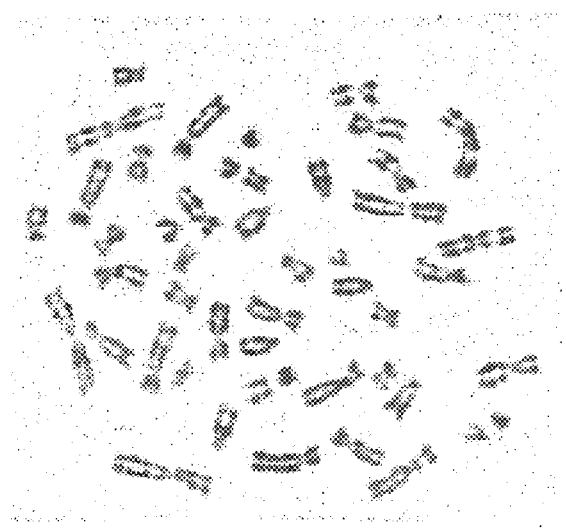
Figure 21D:
Figure 22A:
Figure 22B:
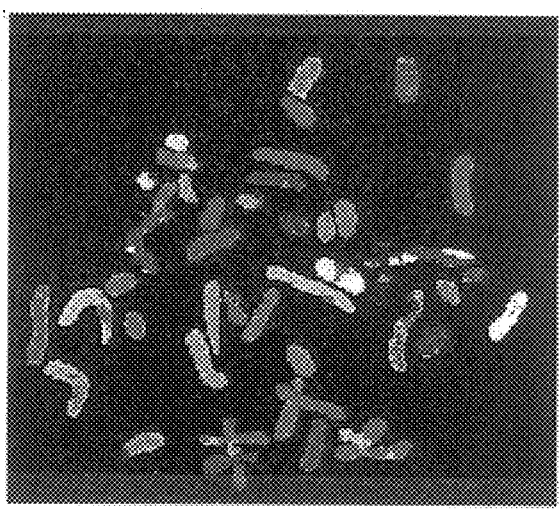
Figure 22C:
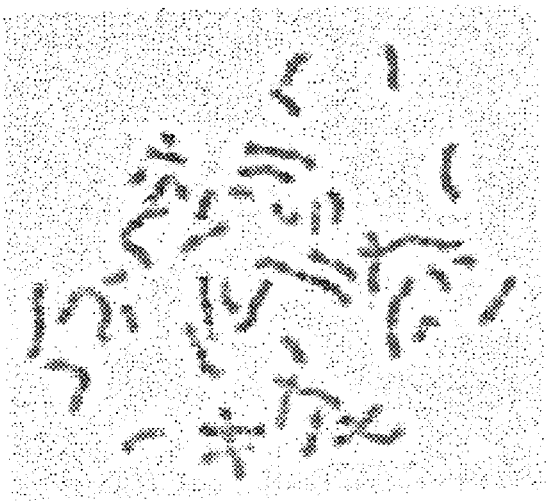
Figure 22D:
Figure 23A:
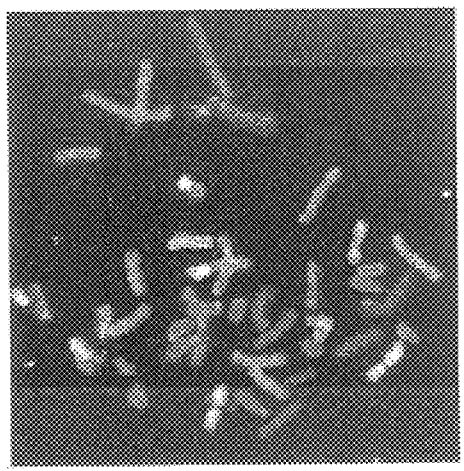
Figure 23B:
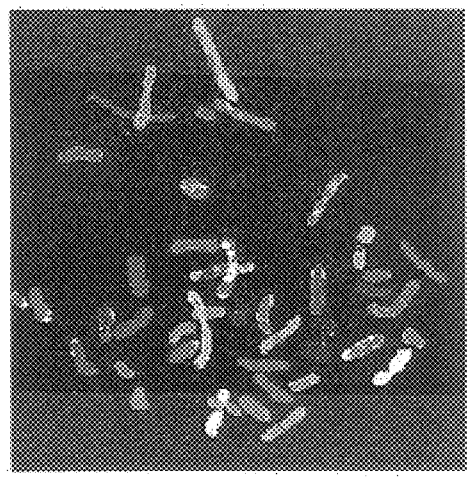
Figure 23C:
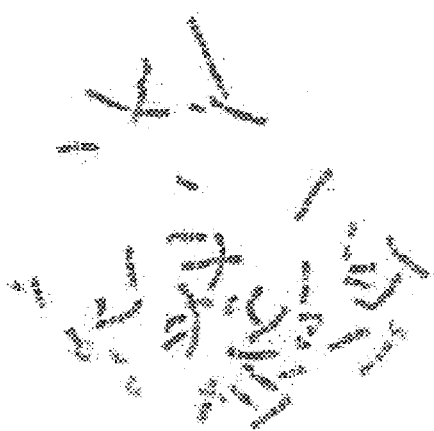
Figure 23D:

FIG. 6 presents an example of the power of this simple algorithm. Consider choosing $\{w_r, w_g, w_b\}$ to be Gaussian or other (e.g., square) functions distributed "inside" a spectrum of interest, the resulting pseudo-color image that is displayed in this case emphasizes only data in the spectral regions corresponding to the weighting functions, enabling spectral differences in these three regions to be detected more clearly.

In FIG. 3, the weighting functions $w_r$, $w_g$, $w_b$, employed were simple square weighting functions, wherein for $w_r$ (red) $\lambda_1$=640 nm and $\lambda_2$=750 nm; for $w_g$ (green) $\lambda_1$=555 nm and $\lambda_2$=640 nm; and for $w_b$ (blue) $\lambda_1$=450 nm and $\lambda_2$=555 nm. The simple weighting functions $w_r$, $w_g$, $w_b$ are integrated to generate an RGB image of the chromosomes.

FIG. 4 is a classification image of the chromosome spread of FIG. 3. FIG. 5 is the karyotype derived from the chromosome spread of FIG. 4. The classification image is calculated by a classification algorithm wherein each pixel is classified according its spectrum. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that a reference spectrum of each chromosome has been measured and stored in a reference library in the computer. A distinguishing classification-color is assigned to each pixel in the image according to the classification-color assigned to the reference spectrum that is most similar to the spectrum at that given pixel, as defined, for example, by a minimal square error algorithm as shown in Equation 3:

$$S_{x,y,n} = \int_{\lambda 1}^{\lambda 2} (I_{x,y}(\lambda) - I_n(\lambda))^2 d\lambda \quad (3)$$

in which $I_{x,y}(\lambda)$ is the normalized spectrum at pixel coordinates x,y and $I_n(\lambda)$ represents the normalized reference spectrum for each of the chromosome n=1, 2, . . . , 23, 24.

After calculating the value of $S_{x,y,n}$ for all reference spectra, the smallest value is chosen and an artificial classification-color is assigned to that pixel in accordance with the classification-color assigned to the most similar reference spectrum.

Please note that the results presented are the product of an unlabeled-Cot-I free hybridization protocol. Indeed, these images slightly differ from similar images obtained in presence of Cot-I. For example, in the RGB image, and to a lesser degree, in the classification image, few of the centromeres, which are known to include high content of highly repetitive sequences, are brighter, indicating that these centromeres have hybridized to repetitive sequences originating from plurality of chromosomes. The color patterns repetitively associated with the telomeres of chromosomes 13, 14, 15 and 21 are due to intermediate repetitive ribosomal DNA sequences residing on these telomeres. These color patterns, which some times also show on chromosome 22, which also contain ribosomal DNA, are observed also in Cot-I including hybridization mixes, since Cot-I is a fraction including mostly highly repetitive sequences, as opposed to intermediate repetitive sequences. These color patterns can be abolished by adding unlabeled ribosomal DNA in excess to the hybridization mix prior to the partial reannealing procedure.

Thus, the in situ hybridization according to the present invention, although unlabeled-Cot-I free, provides high quality karyotype images. Please note that unlabeled-Cot-I free in situ hybridizations with chromosomal paints were never attempted before.

FIGS. 7–23 show RGB (a), classification (b), DAPI (c) and composite karyotypes derived from the RGB and classification images (d) of human male lymphocyte chromosomes, respectively, as retrieved using the SPECTRACUBE system.

In FIGS. 7a–d, the hybridization composite included Cot-I blocking DNA and therefore this result serves as a control. The chromosomal paints were not diluted. The hybridization composite was denatured at 75° C. for 7 minutes and was then left to reanneal for 1 hour at 37° C. prior to hybridization. Hybridization is time was 36 hours. Post wash was with 55% formamide/1× SSC.

In FIGS. 8a–d, the hybridization composite included Cot-I blocking DNA and therefore this result also serves as a control. The chromosomal paints were diluted 1:15 in DENHYB solution. The hybridization composite was denatured at 75° C. for 7 minutes and was then left to reanneal for 1 hour at 37° C. prior to hybridization. Hybridization time was 36 hours. Post wash was with 55% formamide/2× SSC.

In FIGS. 9a–d, the hybridization composite included Cot-I blocking DNA and therefore this result also serves as a control. The chromosomal paints were diluted 1:10 in DENHYB solution. The hybridization composite was denatured at 75° C. for 7 minutes and was then left to reanneal for 1 hour at 37° C. prior to hybridization. Hybridization time was 36 hours. Post wash was with 55% formamide/2× SSC.

In FIGS. 10a–d, the hybridization composite did not include Cot-I blocking DNA. The chromosomal paints were diluted 1:10 in DENHYB solution. The hybridization composite was denatured at 75° C. for 7 minutes and was then left to reanneal for 4 hours at 37° C. prior to hybridization. Hybridization time was 14 hours. Post wash was with 55% formamide/1× SSC.

In FIGS. 11a–d, the hybridization composite did not include Cot-I blocking DNA. The chromosomal paints were diluted 1:10 in DENHYB solution. The hybridization composite was denatured at 75° C. for 7 minutes and was then left to reanneal for 2 hours at 37° C. prior to hybridization. Hybridization time was 14 hours. Post wash was with 55% formamide/1× SSC.

In FIGS. 12a–d, the hybridization composite did not include Cot-I blocking DNA. The chromosomal paints were not diluted. The hybridization composite was denatured at 75° C. for 7 minutes and was then left to reanneal for 2 hours at 37° C. prior to hybridization. Hybridization time was 36 hours. Post wash was with 55% formamide/1× SSC.

In FIGS. 13a–d, the hybridization composite included Cot-I blocking DNA and therefore serves as a control. The chromosomal paints were diluted 1:15 in DENHYB solution. The hybridization composite was denatured at 75° C. for 7 minutes and was then left to reanneal for 1 hour at 37° C. prior to hybridization. Hybridization time was 36 hours. Post wash was with 55% formamide/2× SSC.

In FIGS. 14a–d, the hybridization composite included Cot-I blocking DNA and therefore serves as a control. The chromosomal paints were not diluted. The hybridization composite was denatured at 75° C. for 7 minutes and was then left to reanneal for 1 hour at 37° C. prior to hybridization. Hybridization time was 36 hours. Post wash was with 55% formamide/133 SSC.

In FIGS. 15a–d, the hybridization composite included Cot-I blocking DNA and therefore serves as a control. The chromosomal paints were diluted 1:10 in DENHYB solution. The hybridization composite was denatured at 75° C. for 7 minutes and was then left to reanneal for 1 hour at 37° C. prior to hybridization. Hybridization time was 36 hours. Post wash was with 55% formamide/2× SSC.

In FIGS. 16a–d, the hybridization composite did not include Cot-I blocking DNA. The chromosomal paints were diluted 1:10 in DENHYB solution. The hybridization composite was denatured at 75° C. for 7 minutes and was then left to reanneal for 2 hours at 37° C. prior to hybridization. Hybridization time was 36 hours. Post wash was with 50% formamide/2× SSC.

In FIGS. 17a–d, the hybridization composite did not include Cot-I blocking DNA. The chromosomal paints were diluted 1:10 in DENHYB solution. The hybridization composite was denatured at 75° C. for 7 minutes and was then left to reanneal for 6 hours at 37° C. prior to hybridization. Hybridization time was 36 hours. Post wash was with 55% formamide/1× SSC.

In FIGS. 18a–d, the hybridization composite did not include Cot-I blocking DNA. The chromosomal paints were diluted 1:15 in DENHYB solution. The hybridization composite was denatured at 75° C. for 7 minutes and was then left to reanneal for 2 hours at 37° C. prior to hybridization. Hybridization time was 36 hours. Post wash was with 55% formamide/1× SSC.

In FIGS. 19a–d, the hybridization composite included Cot-I blocking DNA and therefore this result serves as a control. The chromosomal paints were diluted 1:15 in DEN-HYB solution. The hybridization composite was denatured at 75° C. for 7 minutes and was then left to reanneal for 1 hours at 37° C. prior to hybridization. Hybridization time was 36 hours. Post wash was with 55% formamide/2× SSC.

In FIGS. 20a–d, the hybridization composite did not include Cot-I blocking DNA. The chromosomal paints were diluted 1:10 in DENHYB solution. The hybridization composite was denatured at 75° C. for 7 minutes and was then left to reanneal for 2 hours at 37° C. prior to hybridization. Hybridization time was 36 hours. Post wash was with 55% formamide/1× SSC.

In FIGS. 21a–d, the hybridization composite did not include Cot-I blocking DNA. The chromosomal paints were not diluted. The hybridization composite was denatured at 75° C. for 7 minutes and was then left to reanneal for 2 hours at 37° C. prior to hybridization. Hybridization time was 36 hours. Post wash was with 55% formamide/1× SSC.

In FIGS. 22a–d, the hybridization composite did not include Cot-I blocking DNA. The chromosomal paints were diluted 1:10 in DENHYB solution. The hybridization composite was denatured at 75° C. for 7 minutes and was then left to reanneal for 6 hours at 37° C. prior to hybridization. Hybridization time was 36 hours. Post wash was with 55% formamide/1× SSC.

In FIGS. 23a–d, the hybridization composite did not include Cot-I blocking DNA. The chromosomal paints were diluted 1:15 in DENHYB solution. The hybridization composite was denatured at 75° C. for 7 minutes and was then left to reanneal for 2 hours at 37° C. prior to hybridization. Hybridization time was 36 hours. Post wash was with 55% formamide/1× SSC.

The main conclusion derived from the results presented in FIGS. 7–23 is that the chromosome paints concentration can be diluted many folds according to the prior art (including Cot-I blocking DNA) method or the method according to the present invention (Cot-I free) and thereby render the methods costeffective. However, the use of DENHYB™, in combination with the Cot-I free method unexpectedly improves the results apparently because the overall paint concentration is reduced.

FIGS. 24a–b and 25a–b show an image of human chromosomes, hybridized with chromosome 1 or 5 paints, respectively. The chromosome paint of FIGS. 24b and 25b were treated to at least partially remove Cot-I sequences via magnetic beads as described under Example 1 hereinabove, whereas the chromosome paints of FIGS. 24a and 25a were not. In all cases prolonged reannealing (4 hours) served to further reanneal still available labeled Cot-I sequences.

The results show a remarkable improvement in paint specificity. When Cot-I sequences were not removed, the paints highlighted repetitive sequences in substantially all of the other chromosomes, whereas partial removal of Cot-I sequences resulted in chromosome specific hybridization. In FIGS. 24a–b the very same result is shown also for interphase chromosomes.

What is claimed is:

1. A fluorescent in situ hybridization method comprising the steps of:

(a) obtaining a chromosome spread of a species;

(b) preparing a hybridization composite containing a plurality of chromosomal paints each of said plurality of chromosomal paints being labeled with a different fluorophore-or-combination-of-fluorophores, such that an average specific activity of highly repetitive sequences in said hybridization composite substantially equals an average specific activity of unique sequences in said hybridization composite;

(c) denaturing said hybridization composite and subjecting said hybridization composite to conditions for allowing at least a part of said highly repetitive sequences in said hybridization composite to reanneal while at least a part of said unique sequence in said hybridization composite remaining single stranded;

(d) contacting under hybridization conditions said hybridization composite with said spread;

(e) washing away excess of said hybridization composite; and (d) analyzing and presenting images of said now hybridized chromosome spread;

wherein said repetitive sequences present in said plurality of chromosomal paints are at least partially removed from said composite, such that they are under-represented as compared to genomic DNA.

2. The method of claim 1, wherein said species is a mammal.

3. The method of claim 2, wherein said mammal is a human being.

4. The method of claim 1, wherein said hybridization composite contains any number between 1 and all chromosomal paints available for said species.

5. The method of claim 1, wherein at least one of said chromosomal paints is a partial chromosomal paint for painting a specific segment of a chromosome.

6. The method of claim 1, wherein said hybridization composite further includes excess of unlabeled intermediate repetitive sequences.

7. The method of claim 6, wherein said unlabeled intermediate repetitive sequences are ribosomal DNA sequences.

8. The method of claim 1, wherein said chromosome spread is of one species and said chromosomal paints are of another species.

9. The method of claim 1, wherein said hybridization composite further includes a denaturation agent.

10. The method of claim 9, wherein said denaturation agent is formamide.

11. The method of claim 1, wherein said hybridization composite further includes a polymer.

12. The method of claim 11, wherein said polymer is Dextran sulfate.

13. The method of claim 1, wherein said hybridization composite further includes salts.

14. The method of claim 13, wherein said salts are SSC.

15. The method of claim 1, wherein said averaged specific activities fall within a range of 1–25 fluorophores per 100 nucleotides.

16. The method of claim 1, wherein said conditions allowing at least a part of said highly repetitive sequences in said hybridization composite to reanneal are within a range of about 32–36° C. for about 2–4 hours.

17. The method of claim 1, wherein said hybridization conditions include a temperature of about 37° C. for a period of time sufficient for said unique sequences of said chromosomal paints to hybridize with their corresponding sequences in said chromosome spread.

18. The method of claim 1, wherein said washing step is effected in part by diluted SSC solution.

19. The method of claim 1, wherein analyzing and presenting images of said now hybridized chromosome spread is effected by multi-band light collection device or a spectral imager.

20. The method of claim 19, wherein said spectral imager includes an interferometer.

21. The method of claim 1, wherein each of said chromosomal paints is prepared by labeling with said fluorophores a PCR product derived from a sorted chromosome.

22. The method of claim 1, wherein each of said chromosomal paints is prepared by labeling with said fluorophores a sorted chromosome.

23. A fluorescent in situ hybridization method comprising the steps of:

(a) obtaining a chromosome spread of a species;

(b) preparing an unlabeled-Cot-I free hybridization composite containing a plurality of chromosome paints each of said plurality of chromosomal paints being labeled with a different fluorophore-or-combination-of-fluorophores;

(c) denaturing said hybridization composite and subjecting said hybridization composite to conditions for allowing mostly highly repetitive sequences in said hybridization composite to reanneal while preserving unique sequences in said in said hybridization composite mostly single stranded;

(d) contacting under hybridization conditions said hybridization composite with said spread;

(e) washing away excess of said hybridization composite; and (d) analyzing and presenting images of said now hybridized chromosome spread;

wherein said repetitive sequences present in said plurality of chromosomal paints are at least partially removed from said composite, such that they are under-represented as compared to genomic DNA.

24. The method of claim 23, wherein said species is a mammal.

25. The method of claim 24, wherein said mammal is a human being.

26. The method of claim 23, wherein said hybridization composite contains any number between 1 and all chromosomal paints available for said species.

27. The method of claim 23, wherein at least one of said chromosomal paints is a partial chromosomal paint for painting a specific segment of a chromosome.

28. The method of claim 23, wherein said hybridization composite further includes excess of unlabeled intermediate repetitive sequences.

29. The method of claim 28, wherein said unlabeled intermediate repetitive sequences are ribosomal DNA sequences.

30. The method of claim 23, wherein said chromosome spread is of one species and said chromosomal paints are of another species.

31. The method of claim 23, wherein said hybridization composite further includes a denaturation agent.

32. The method of claim 31, wherein said denaturation agent is formamide.

33. The method of claim 23, wherein said hybridization composite further includes a polymer.

34. The method of claim 33, wherein said polymer is Dextran sulfate.

35. The method of claim 23, wherein said hybridization composite further includes salts.

36. The method of claim 35, wherein said salts are SSC.

37. The method of claim 23, wherein said conditions allowing at least a part of said highly repetitive sequences in said hybridization composite to reanneal are within a range of about 32–36° C. for about 2–4 hours.

38. The method of claim 23, wherein said hybridization conditions include a temperature of about 37° C. for a period of time sufficient for said unique sequences of said chromosomal paints to hybridize with their corresponding sequences in said chromosome spread.

39. The method of claim 23, wherein said washing step is effected in part by diluted SSC solution.

40. The method of claim 23, wherein analyzing and presenting images of said now hybridized chromosome spread is effected by multi-band light collection device or a spectral imager.

41. The method of claim 40, wherein said spectral imager includes an interferometer.

42. The method of claim 23, wherein each of said chromosomal paints is prepared by labeling with said fluorophores a PCR product derived from a sorted chromosome.

43. The method of claim 23, wherein each of said chromosomal paints is prepared by labeling with said fluorophores a sorted chromosome.

44. A hybridization composite comprising a plurality of chromosomal paints each of said plurality of chromosomal paints being labeled with a different fluorophore-or-combination-of-fluorophores, such that an averaged specific activity of highly repetitive sequences in the hybridization composite substantially equals an averaged specific activity of unique sequences in said hybridization composite, wherein said repetitive sequences present in said plurality of chromosomal paints are at least partially removed from said composite, such that they are under-represented as compared to genomic DNA.

45. The hybridization composite of claim 44, wherein highly repetitive sequences in the hybridization composite are mostly annealed whereas unique sequences in said hybridization composite are mostly single stranded.

46. The hybridization composite of claim 45, wherein when the hybridization composite is allowed to hybridize with a chromosome spread, chromosomes or parts thereof having matching chromosomal paints are labeled and are analyzable via a spectral imager or a multi-band light collection device.

47. The hybridization composite of claim 44, further comprising a denaturing agent.

48. The hybridization composite of claim 47, wherein said denaturation agent is formamide.

49. The hybridization composite of claim 44, further comprising a polymer.

50. The hybridization composite of claim 49, wherein said polymer is Dextran sulfate.

51. The hybridization composite of claim 44, further comprising salts.

52. The hybridization composite of claim 51, wherein said salts are SSC.

53. The hybridization composite of claim 44, wherein each of said chromosomal paints is prepared by labeling with said fluorophores a PCR product derived from a sorted chromosome.

54. The hybridization composite of claim 44, wherein each of said chromosomal paints is prepared by labeling with said fluorophores a sorted chromosome.

55. A hybridization composite comprising a plurality of chromosomal paints each of said plurality of chromosomal paints being labeled with a different fluorophore-or-combination-of-fluorophores, such that an averaged specific activity of highly repetitive sequences in the hybridization composite substantially equals an averaged specific activity of unique sequences in said hybridization composite, wherein highly repetitive sequences in the hybridization composite are mostly annealed, whereas unique sequences in said hybridization composite are mostly single stranded, such that when the hybridization composite is allowed to hybridize with a chromosome spread, chromosomes or parts thereof having matching chromosomal paints are labeled and are analyzable via a spectral imager or a multi-band light collection device, wherein said repetitive sequences present in said plurality of chromosomal paints are at least partially removed from said composite, such that they are under-represented as compared to genomic DNA.

56. The hybridization composite of claim 55, further comprising a denaturing agent.

57. The hybridization composite of claim 56, wherein said denaturation agent is formamide.

58. The hybridization composite of claim 55, further comprising a polymer.

59. The hybridization composite of claim 58, wherein said polymer is Dextran sulfate.

60. The hybridization composite of claim 55, further comprising salts.

61. The hybridization composite of claim 60, wherein said salts are SSC.

62. The hybridization composite of claim 55, wherein each of said chromosomal paints is prepared by labeling with said fluorophores a PCR product derived from a sorted chromosome.

63. The hybridization composite of claim 55, wherein each of said chromosomal paints is prepared by labeling with said fluorophores a sorted chromosome.

64. A hybridization composite consisting essentially of a plurality of chromosomal paints each of said plurality of chromosomal paints being labeled with a different fluorophore-or-combination-of-fluorophores, such that an averaged specific activity of highly repetitive sequences in the hybridization composite substantially equals an averaged specific activity of unique sequences in said hybridization composite, wherein highly repetitive sequences in the hybridization composite are mostly annealed, whereas unique sequences in said hybridization composite are mostly single stranded, such that when the hybridization composite is allowed to hybridize with a chromosome spread, chromosomes or parts thereof having matching chromosomal paints are labeled and are analyzable via a spectral imager or a multi-band light collection device, said hybridization composite further consisting of a denaturing agent, a polymer and salts, wherein said repetitive sequences present in said plurality of chromosomal paints are at least partially removed from said composite, such that they are under-represented as compared to genomic DNA.

65. The hybridization composite of claim 64, wherein each of said chromosomal paints is prepared by labeling with said fluorophores a PCR product derived from a sorted chromosome.

66. The hybridization composite of claim 64, wherein each of said chromosomal paints is prepared by labeling with said fluorophores a sorted chromosome.

* * * * *

SEQUENCE LISTING (1) GENERAL INFORMATION:

(iii) NUMBER OF SEQUENCES:1

```
(2) INFORMATION FOR SEQ ID NO:1:

(i) SEQUENCE CHARACTERISTICS:
        (A) LENGTH:        22
        (B) TYPE:          nucleic acid
        (C) STRANDEDNESS:  single
        (D) TOPOLOGY:      linear (xi) SEQUENCE DESCRIPTION: SEQ ID NO:1:

CCGACTCGAG NNNNNNATGT GG                                                    22
```